US007251893B2

(12) United States Patent
Cohen et al.

(10) Patent No.: US 7,251,893 B2
(45) Date of Patent: Aug. 7, 2007

(54) TRIBOLOGICAL APPLICATIONS OF POLYELECTROLYTE MULTILAYERS

(75) Inventors: Robert E. Cohen, Jamaica Plain, MA (US); Prem V. Pavoor, Somerville, MA (US); Anuj Bellare, Brighton, MA (US); Brian P. Gearing, Berkeley, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 363 days.

(21) Appl. No.: 10/453,453

(22) Filed: Jun. 3, 2003

(65) Prior Publication Data

US 2004/0249469 A1 Dec. 9, 2004

(51) Int. Cl.
  *B21D 53/10* (2006.01)
  *B23P 19/04* (2006.01)
  *A61F 2/30* (2006.01)
(52) U.S. Cl. .................. 29/898.13; 623/23.6; 29/460
(58) Field of Classification Search ............ 29/898.13, 29/460; 623/23.6, 908; 428/461, 441, 426, 428/457, 500
  See application file for complete search history.

(56) References Cited

U.S. PATENT DOCUMENTS

| 3,619,248 | A | * | 11/1971 | Whitsitt et al. ............. 428/451 |
| 3,756,992 | A | * | 9/1973 | Dieterich ..................... 524/591 |
| 4,522,453 | A | | 6/1985 | Lammer et al. ............ 308/3 R |
| 4,571,358 | A | | 2/1986 | Suh et al. ................... 428/155 |
| 5,038,625 | A | | 8/1991 | Chen .......................... 73/865.9 |
| 5,504,139 | A | | 4/1996 | Davies et al. ............... 524/504 |
| 5,538,649 | A | | 7/1996 | Demendi et al. ........... 508/101 |
| 5,540,750 | A | | 7/1996 | Fernandez et al. ............ 75/235 |
| 5,670,586 | A | | 9/1997 | Ash et al. .................... 525/539 |
| 5,679,883 | A | | 10/1997 | Wedeven ....................... 73/10 |
| 5,750,620 | A | | 5/1998 | Davies et al. ................ 525/67 |
| 5,786,076 | A | | 7/1998 | Ederyd et al. .............. 428/325 |

(Continued)

OTHER PUBLICATIONS

Lvov, Y. et al, "Assembly, Structural Characterization and Thermal Behavior of Layer-by-Layer Deposited Ultrathin Films of Poly(vinyl sulfate) and Poly(allyamine)" Langmuir, 1993 (Abstract).*

(Continued)

*Primary Examiner*—John C. Hong
(74) *Attorney, Agent, or Firm*—Dana M. Gordon; Foley Hoag LLP

(57) ABSTRACT

One aspect of the present invention relates to an implantable medical device comprising a surface coated with a polyelectrolyte multilayer, wherein said surface is glass, metal, plastic, polymer, or fiberglass. Another aspect of the present invention involves a method of preparing a PEM-coated implantable medical device, comprising the step of applying a film to a surface of an implantable medical device, wherein said film comprises a polyelectrolyte multilayer and said surface is glass, metal, plastic, polymer, or fiberglass. Another aspect of the present invention involves a method of reducing the wear between two contacting materials, comprising the step of moving a first material in contact with a second material in an environment, wherein a first surface of said first material is in contact with a second surface of said second material, wherein said first surface, said second surface, or both is coated with a polyelectrolyte multilayer, thereby decreasing the wear of said first material, said second material, or both compared to the wear in the absence of said polyelectrolyte multilayer.

30 Claims, 14 Drawing Sheets

Substrate

—— PAH ⊕   ······ PAA

Schematic of the interpenetrated bulk structure of PEMs. Solid lines represent PAH, and dashed lines represent PAA

U.S. PATENT DOCUMENTS

| | | | |
|---|---|---|---|
| 5,925,315 A | 7/1999 | Bourkhina | 420/530 |
| 5,935,378 A | 8/1999 | Wolki et al. | 156/425 |
| 6,191,204 B1 | 2/2001 | Johnson | 524/439 |
| 6,228,310 B1 | 5/2001 | Johnson | 264/331.11 |
| 6,228,444 B1 | 5/2001 | Wolki et al. | 428/34.4 |
| 6,258,870 B1* | 7/2001 | Hubbell et al. | 522/26 |
| 6,316,084 B1* | 11/2001 | Claus et al. | 428/212 |
| 6,319,583 B1 | 11/2001 | Chen | 428/64.3 |
| 6,515,254 B2 | 2/2003 | Beck et al. | 219/121.69 |
| 6,520,703 B1 | 2/2003 | Narasimhan et al. | 403/29 |
| 6,596,792 B2 | 7/2003 | Johnson | 524/80 |
| 6,641,322 B2 | 11/2003 | Narasimhan et al. | 403/29 |
| 6,641,893 B1 | 11/2003 | Suresh et al. | 428/105 |
| 6,881,444 B2* | 4/2005 | Hong et al. | 427/240 |
| 6,926,965 B2* | 8/2005 | Qiu et al. | 428/411.1 |
| 6,940,580 B2* | 9/2005 | Winterton et al. | 428/508 |
| 2001/0023859 A1 | 9/2001 | Beck et al. | 219/121.69 |
| 2002/0028869 A1 | 3/2002 | Johnson | 524/439 |
| 2002/0069819 A1 | 6/2002 | Heinemann et al. | 118/50.1 |
| 2003/0043509 A1 | 3/2003 | Gillis et al. | 360/254.2 |
| 2003/0099509 A1 | 5/2003 | Narasimhan et al. | 403/359.1 |

OTHER PUBLICATIONS

Cho, J. et al, "Fabrication of Highly Ordered Multilayered Films sing a Spin Self-Assembly Method." Advanced. Materials, 13, No. 14 Jul. 18, 2001, 1076-78.*

Pavoor, P. et al, "Ultra-thin polyelectrolyte coating for othopaedic applications." Polymeric Materials Science and Engineering, vol. 87, Fall 2002, Abstract.*

United States Statutory Invention Registration, Registration No.: H174, Published: Feb. 2, 1999, Author: Wakker, Title : Tribological Arrangement, Filed: Sep. 21, 1995.

* cited by examiner

Poly(acrylic acid)
(PAA)

Poly(allylamine hydrochloride)
(PAH)

Structures of repeat units of the polyelectrolytes used for PEM assembly

Substrate

——— PAH ⊕          ▪▪▪▪▪▪▪ PAA

Schematic of the interpenetrated bulk structure of PEMs. Solid lines represent PAH, and dashed lines represent PAA Upper, smaller stationary pin Lower, larger slider surface Pictorial representation of the mating surfaces used in the flexure-based biaxial apparatus Friction profile for an uncoated tool steel pin slid against an uncoated stainless steel substrate. Normal stress 1 MPa based on diameter of pin Optical micrographs and cross-sectional surface profiles of wear tracks after macroscale pin-on-disk tests (2000 cycles).

Plain steel

Steel + (PAH 7.5 / PAA 3.5) 100 nm
Heated at 130 °C a) Plain glass substrate b) Glass substrate coated with 70 nm PEM (PAA/PAH)

US 7,251,893 B2

TRIBOLOGICAL APPLICATIONS OF POLYELECTROLYTE MULTILAYERS

GOVERNMENT SUPPORT

This invention was made with support provided by the National Science Foundation (Grant No. DMR 98-08941); therefore, the government has certain rights in the invention.

BACKGROUND OF THE INVENTION

Over the past several decades, much investigation has been focused on understanding the mechanisms of friction, particularly as arising with respect to two contacting sliding surfaces. The causes of friction between sliding surfaces is discussed, for example, in the article "The Genesis of Friction" by N. P. Suh and H. C. Sin, WEAR, 69 (1981) 91-114. In general, the friction coefficient is not an inherent material property, but is composed of three principal components: one due to the deforming asperities (roughness) of the surface, another due to plowing of the surface by wear particles, and another due to adhesion. Further study has shown that the significance of wear effects can be severe for many materials, such as plastic materials, wherein interfacial wear debris is generated between the two contacting surfaces. The presence of interfacial debris has been shown to have significant adverse effects on the friction coefficient as well as on other related wear behavior. For example, the interfacial wear debris derived from polymer-based materials can contribute appreciably to the total friction coefficient.

Attempts to reduce the coefficient of friction and maintain a constant coefficient of friction between two substrates have been reported. One approach involves applying a lubricant, or grease-like substance between the sliding surfaces. Although such approaches work well in some instances, in many applications the presence of such lubricants, either separately or incorporated in the material itself, cannot be tolerated since they may introduce undesired contaminants or other undesired physical characteristics into the process or device in which the sliding surfaces are used. For example, the use of lubricants in food processing, photocopying, or orthopedic applications is not constructive owing to contamination concerns. Hence, it is desirable that a technique be developed for avoiding the use of lubricants while still maintaining a substantially constant coefficient of friction over a reasonable length of time, particularly where deleterious amounts of wear debris are generated during use.

The need for external lubricants may be reduced or eliminated by the use of polymeric contacting components. Polymeric contact components may be fabricated by applying a film of polymeric material to the surface of a substrate. Alternatively, polymeric components may be manufactured by injection molding to form intricately shaped components such as gears, cams, bearings, slides, ratchets, pumps, electrical contacts and prostheses. Polymeric contacting components provide an economical and essentially maintenance free method to reduce friction between two sliding contacting surfaces. Components formed from polymeric compounds have greater shock and vibration dampening, reduced weight, enhanced corrosion protection, decreased running noise, decreased maintenance and power use, and allow increased freedom of component design over non-polymeric components.

U.S. Pat. No. 4,174,358 discloses toughened thermoplastic compositions having a polyamide matrix resin and at least one branched or straight chain toughening polymer. The polymer may be elastomeric or thermoplastic. Examples of suitable toughening polymers include synthetic and natural rubbers such as styrene/butadiene rubber, isobutylene, isoprene, natural rubber, ethyl acrylate, butyl acrylate rubbers, etc.

U.S. Pat. No. 4,371,445 discloses tribological systems of plastic/plastic pairings in which at least one of the partners is a plastic containing polar, cyclic compounds. The cyclic part of the molecule on at least one side may be coupled directly to an atom of Group V or Group VI of the Periodic Table or the ring may contain atoms of Group V or VI. An optional auxiliary sliding partner may be formed from a polyalkylene. A partner may consist of several materials, such as a mixture of two or more of polyethylene, polypropylene, polyisobutylene, polystyrene, polytetrafluoroethylene and polyvinylidene chloride.

U.S. Pat. No. 4,987,170 discloses a styrene resin composition including styrene polymer, dimethylsilicone oil and a maleic anhydride monomer or a maleic anhydride-styrene copolymer. The styrene polymer may be modified with a rubber-like polymer, such as polybutadiene, styrene-butadiene copolymer, butadiene-acrylonitrile copolymer, ethylenepropylene-diene terpolymers and butadiene-acrylate copolymers.

One class of polymers that could be used to improve sliding properties and increase wear resistance between two sliding contacting surfaces is polyelectrolyte multilayers (PEMs). These polymers may be prepared using a layer-by-layer assembly technique introduced by Decher. See Decher, G.; Hong, J.-D. *Makromol. Chem., Macromol. Symp.* 1991, 46, 321-327; Decher, G.; Hong, J.-D. *Ber. Bunsenges. Phys. Chem.* 1991, 95, 1430-1434; and Decher, G.; Hong, J. D.; Schmitt, J. *Thin Solid Films* 1992, 210/211, 831. This approach, which utilizes electrostatic interactions between oppositely charged polyion species to create alternating layers of sequentially adsorbed polyions, provides a simple and elegant means of depositing layer-by-layer sub-nanometer-thick polymer films onto a surface using aqueous solutions. Lvov, Y. M.; Decher, G. *Crystallography Reports* 1994, 39, 628-647; Ferreira, M.; Rubner, M. F. *Macromol.* 1995, 28, 7107-7114; and Tsukruk, V. V.; Rinderspacher, F.; Bliznyuk, V. N. *Langmuir* 1997, 13, 2171-2176. Recently, PEMs have been used in electroluminescent LEDs, conducting polymer composites, assembly of proteins and metal nanoparticle systems, thin film optoelectronic devices, and nanostructured thin film coatings. See Decher, G. *Science* 1997, 277, 1232; Tian, J.; Wu, C. C.; Thompson, M. E.; Sturm, J. C.; Register, R. A.; Marsella, M. J.; Swager, T. M. *Adv. Mater.* 1995, 7, 395; Baur, J. W.; Kim, S.; Balanda, P. B.; Reynolds, J. R.; Rubner, M. F. *Advanced Materials* 1998, 10, 1452-1455; Ferreira, M.; Cheung, J. H.; Rubner, M. F. *Thin Solid Films* 1994, 244, 806-809; and Ariga, K.; Lvov, Y.; Onda, M.; Ichinose, I.; Kunitake, T. *Chemistry Letters* 1997, 125-126. Despite the significant interest in polyelectrolyte multilayer films, the tribological properties of these materials have not been thoroughly investigated. Consequently, the present invention reveals that polyelectrolyte multilayer films display a significant capacity for wear prevention, thereby helping to solve the longstanding problem of reducing wear associated with movement along two surfaces.

Surface engineering, via thin organic films offers the potential for wear reduction in total joint replacement prostheses. Orthopedic implants, with metal-on-plastic configurations, have employed an ultra-high molecular weight polyethylene (UHMWPE) bearing surface for almost four decades. The life of the implant is limited by the wear of UHMWPE; the wear debris induces bone resorption through a biological reaction, causing implant loosening, and necessitating a revision surgery. Currently, no satisfactory procedures have been determined to combat the wear problems of orthopedic implants comprising UHMWPE. Therefore, it would be highly desirable to develop a highly durable polymeric film that could be used to coat joint replacement prostheses.

Surface modification has also received a large amount of attention in the case of micromotors, gear trains, mechanical relays, valves, and other devices in MEMS. See S. Sundararajan and B. Bhushan, Micro/nanoscale tribology of MEMS materials, lubricants and devices, in: B. Bhushan (Ed.), NATO advances study institute on fundamentals of tribology and bridging the gap between the macro- and micro/nano scales, Kluwer Academic Publishers, Keszthely, Hungary, 821-850, 2000. The factors impeding reliable operation of these devices include wear of the silicon-based materials, high friction forces, and stiction between the mating surfaces. See K. Komvopoulos *Wear* 1996, 200, 305-327. A number of organic coatings have been studied with respect to friction, stiction, and wear reduction in these devices, including Langmuir monolayers (See V. V. Tsukruk, V. N. Bliznyuk, J. Hazel, D. Visser and M. P. Everson *Langmuir* 1996, 12, 4840-4849), self-assembled monolayers (See S. Sundararajan and B. Bhushan, Micro/nanoscale tribology of MEMS materials, lubricants and devices, in: B. Bhushan (Ed.), NATO advances study institute on fundamentals of tribology and bridging the gap between the macro- and micro/nano scales, Kluwer Academic Publishers, Keszthely, Hungary, 821-850, 2000; and V. DePalma and N. Tillman *Langmuir* 1989, 5, 868-872), and polymer films with layered architectures. See D. Julthingpiput, H. Ahn, D. Kim and V. V. Tsukruk *Tribology Letters* 2002, 13, 35-40 and A. Sidorenko, H. Ahn, D. Kim, H. Yang and V. V. Tsukruk *Wear* 2002, 252, 946-955. Most of these coatings require either an intricate protocol for assembly, or a large density of functional groups by which they can covalently bind to the substrate. Release of corrosive by-products, and polymerization of precursor molecules leading to particulate formation, are some examples of other problems encountered during processing of these films. See R. Maboudian, W. R. Ashurst and C. Carraro *Tribology Letters* 2002, 12, 95-100 These issues are not encountered during processing of PEMs. Consequently, PEMs may present a facile solution to the tribological issues facing MEMS.

SUMMARY OF THE INVENTION

One aspect of the present invention generally relates to an implantable medical device comprising a surface coated with a polyelectrolyte multilayer, wherein said surface is glass, metal, plastic, polymer, or fiberglass. In certain embodiments, the polyelectrolyte multilayer comprises a linear or branched poly(acrylic acid) or poly(allylamine hydrochloride). In certain embodiments, the surface is metal, plastic, or polymer. In a preferred embodiment, the surface is stainless steel or ultra-high molecular weight polyethylene. In certain embodiments, the surface is metal and said polyelectrolyte multilayer comprises poly(acrylic acid). In certain embodiments, the polyelectrolyte multilayer is less than about 700 nm thick. In a preferred embodiment, the polyelectrolyte multilayer is less than about 500 nm thick. In certain embodiments, the polyelectrolyte multilayer is less than about 100 nm thick. In certain embodiments, the polyelectrolyte multilayer is less than about 10 nm thick. In certain embodiments, the polyelectrolyte multilayer further comprises a metallic nanocluster. In a preferred embodiment, the implantable medical device is a ball and socket joint. In certain embodiments, the implantable medical device is a ball and socket joint, the polyelectrolyte multilayer comprises poly(acrylic acid) and poly(allylamine hydrochloride). In certain embodiments, the implantable medical device is a ball and socket joint and the polyelectrolyte multilayer comprises poly(acrylic acid) and poly(allylamine hydrochloride), and the surface is ultra-high molecular weight polyethylene.

Another aspect of the present invention involves a method of preparing a PEM-coated implantable medical device, comprising the step of applying a film to a surface of an implantable medical device, wherein said film comprises a polyelectrolyte multilayer and said surface is glass, metal, plastic, polymer, or fiberglass. In certain embodiments, the film comprises a linear or branched poly(acrylic acid) or poly(allylamine hydrochloride). In certain embodiments, the surface is metal, plastic, or polymer. In certain embodiments, the surface is stainless steel or ultra-high molecular weight polyethylene. In certain embodiments, the surface is metal and said film comprises poly(acrylic acid). In certain embodiments, the film is less than about 700 nm thick. In a preferred embodiment, the film is less than about 500 nm thick. In certain embodiments, the film is less than about 100 nm thick, or 10 nm thick. In certain embodiments, the film comprises a polyelectrolyte multilayer and a metallic nanocluster. In a preferred embodiment, the film comprises a polyelectrolyte multilayer and a silver nanocluster. In certain embodiments, the implantable medical device is a ball and socket joint.

Another aspect of the present invention involves a method of reducing the wear between two contacting materials, comprising the step of moving a first material in contact with a second material in an environment, wherein a first surface of said first material is in contact with a second surface of said second material, wherein said first surface, said second surface, or both is coated with a polyelectrolyte multilayer, thereby decreasing the wear of said first material, said second material, or both compared to the wear in the absence of said polyelectrolyte multilayer. In certain embodiments, the polyelectrolyte multilayer comprises a linear or branched poly(acrylic acid) or poly(allylamine hydrochloride). In certain embodiments, the first material is glass, metal, plastic, or polymer. In a preferred embodiment, the first material is metal or plastic. In certain embodiments, the first material is ultra-high molecular weight polyethylene. In certain embodiments, the second material is glass, metal, plastic, or polymer. In certain embodiments, the first material is glass and said second material is metal. In certain embodiments, the first material is plastic and said second material is plastic. In certain embodiments, the first material is plastic and said second material is metal. In certain embodiments, the first material is glass and said polyelectrolyte multilayer comprises poly(acrylic acid). In certain embodiments, the first material is glass and said polyelectrolyte multilayer comprises poly(acrylic acid) and poly(allylamine hydrochloride). In certain embodiments, the first material is metal and said polyelectrolyte multilayer comprises poly(acrylic acid). In certain embodiments, the first material is plastic and said polyelectrolyte multilayer comprises poly(acrylic acid). In certain embodiments, the distal surface of said polyelectrolyte multilayer comprises PAH. In certain embodiments, the first surface and said second surface is coated with a polyelectrolyte multilayer. In certain embodiments, the first surface and the second surface is coated with a polyelectrolyte multilayer comprising poly(acrylic acid). In a preferred embodiment, the first material is metal, said second material is plastic, and said first surface is coated with a polyelectrolyte multilayer. In certain embodiments, the first material is plastic, the second material is plastic, and the first surface is coated with a polyelectrolyte multilayer. In a preferred embodiment, the first material is glass, the second material is metal, and the first surface and the second surface is coated with a polyelectrolyte multilayer. In certain embodiments, the first material is plastic, said second material is plastic, and said first surface and the second surface is coated with a polyelectrolyte multilayer. In certain embodiments, the first material is metal, said second material is plastic, and said first surface is coated with a polyelectrolyte multilayer comprising poly(acrylic acid). In certain embodiments, the polyelectrolyte multilayer is less than about 700 nm thick. In a preferred embodiment, the polyelectrolyte multilayer is less than about 500 nm thick. In certain embodiments, the polyelectrolyte multilayer is less than about 100 nm thick or 10 nm thick. In certain embodiments, the polyelectrolyte multilayer further comprises a metallic nanocluster. In a preferred embodiment, the polyelectrolyte multilayer further comprises a silver nanocluster. In certain embodiments, the environment comprises water or bovine calf serum. In a preferred embodiment, the environment comprises synovial joint fluid.

DETAILED DESCRIPTION OF THE INVENTION

Figure 1:
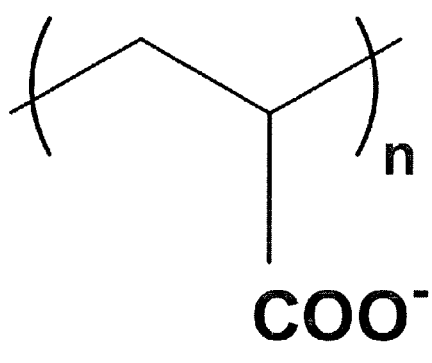
FIG. 1 depicts structures of repeat units of certain polyelectrolytes used for PEM assembly.
Figure 1:
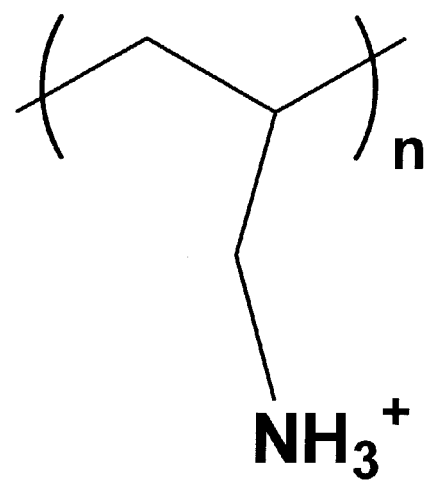

The invention will now be described more fully with reference to the accompanying examples, in which certain preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Overview of a Preferred Embodiment

A number of organic coatings have been studied with respect to friction, stiction, and wear reduction in devices, including Langmuir monolayers (See V. V. Tsukruk, V. N. Bliznyuk, J. Hazel, D. Visser and M. P. Everson *Langmuir* 1996, 12, 4840-4849), self-assembled monolayers (See S. Sundararajan and B. Bhushan, Micro/nanoscale tribology of MEMS materials, lubricants and devices, in: B. Bhushan (Ed.), NATO advances study institute on fundamentals of tribology and bridging the gap between the macro- and micro/nano scales, Kluwer Academic Publishers, Keszthely, Hungary, 821-850, 2000; and V. DePalma and N. Tillman *Langmuir* 1989, 5, 868-872), and polymer films with layered architectures. See D. Julthingpiput, H. Ahn, D. Kim and V. V. Tsukruk *Tribology Letters* 2002, 13, 35-40 and A. Sidorenko, H. Ahn, D. Kim, H. Yang and V. V. Tsukruk *Wear* 2002, 252, 946-955. Most of these coatings require either an intricate protocol for assembly, or a large density of functional groups by which they can covalently bind to the substrate. Release of corrosive by-products and polymerization of precursor molecules leading to particulate formation are examples of other problems encountered during processing of these films. See R. Maboudian, W. R. Ashurst and C. Carraro *Tribology Letters* 2002, 12, 95-100 These issues are not encountered during processing of PEMs. The films obviate the need for elaborate pretreatment steps, and can be assembled on a wide variety of materials. In addition, no corrosive by-products are formed during processing. Hence, PEMs are a promising approach to wear prevention.

One aspect of the present invention relates to a method of reducing wear between a first material and second material that come into contact, comprising the step of applying a polyelectrolyte multilayer film to the surface of the first material. In certain embodiments, the first and second material are glass, metal, plastic, or polymer. In a preferred embodiment, the PEM comprises poly(acrylic acid) or poly(allylamine hydrochloride). The PEM film is prepared by exposing the surface of the material to alternating solutions of a polyanion, e.g., poly(acrylic acid), and polycation, e.g., poly(allylamine hydrochloride).

The properties of the multilayer can be tuned to meet the needs of a given application. For example, the thickness of the multilayer is determined by the number of polymeric layers applied to the surface of the material. In addition, the pH of the polyanion or polycation solution has been shown to influence the properties of the multilayer film. In one embodiment wherein both the first and second materials are metal, a PEM thickness of approximately 500 nm gave good reduction in wear. In certain embodiments, it is preferable that the surface of polyelectrolyte multilayer distal to the material to which it is bound comprises PAH. It was found that PEMs in which the surface of the multilayer was PAH gave lower friction coefficients. Another advantage is that PEMs provide conformal nanocoatings for a variety of substrates with little or no pretreatment.

Investigation of the tribological properties of PAH-PAA PEMs using a biaxial apparatus and a pin-on-disk tester revealed that the "true" values of friction coefficient for PEM constructs (on steel) against glass, in the absence of substrate wear, were higher than those exhibited by the bare substrates. It is hypothesized that an entangled structure, adhesion, slight asperity penetration, or deformation of the films were the principal causes. The coefficient of friction decreased with increasing normal stress, as expected for polymeric materials.

In certain embodiments, the second material is coated with a polyelectrolyte multilayer film. In a preferred embodiment, the second material is coated with a polyelectrolyte multilayer film comprising poly(acrylic acid) and poly(allylamine hydrochloride).

PEM constructs demonstrated a significant capacity for substrate wear prevention. In certain embodiments, a minimum thickness of the film, depending on the substrate roughness, is optimal for consistent wear prevention without a significant increase in friction force. Tests on a macroscale revealed that wear of glass substrates was prevented even after 2000 cycles. It is proposed that the film fragments prevented contact between the mating surfaces when PEMs are assembled on the larger surface. Deformation and dragging of these fragments, in conjunction with adhesion to the contacting surfaces, are the principal causes of friction forces at these higher stresses. Evidence of the role of PEM fragments in wear reduction was gleaned when PEMs were built on both mating surfaces. In this case, the film fragments from the slider adhered to the film on the stationary pin leading to wear prevention when contact was re-established during a second run. This assembly is especially useful for intermittent contact type situations, where contact may not be re-established at the point of severance. When assembled only on the pin, these films prevented wear of the substrate; the friction coefficient also remained close to that of the bare substrate (prior to the onset of wear).

In certain embodiments, the present invention relates to a method of using PEM films in the presence of water to prevent wear. Experimental results using reciprocating motion indicated that a PAA/PAH film serves to prevent wear of steel substrates in the presence of water and bovine calf serum. The latter simulates joint synovial fluid present if the PEM film were to be used to prevent wear of a prosthetic group. In certain embodiments, the present invention relates to a method of using PEM films in the presence of bovine calf serum to prevent wear.

Dry State Normal Load Analysis

Figure 4:
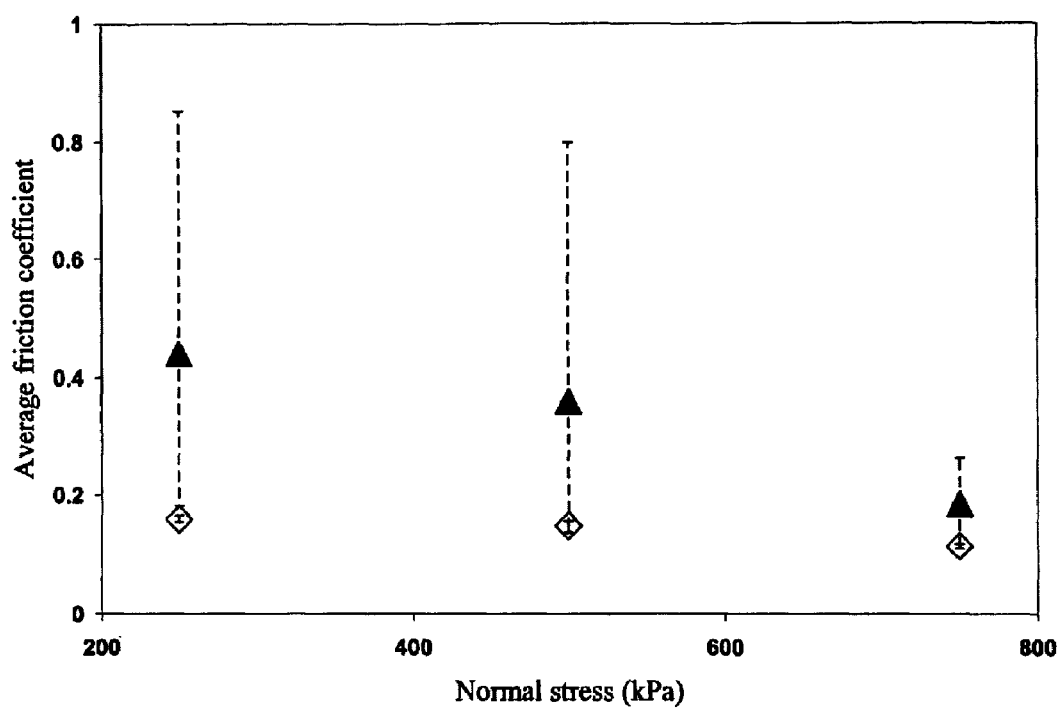
FIG. 4 depicts the average coefficients of friction for an uncoated stainless steel pin (diamonds), and a (PAH 7.5/PAA 3.5) 500 nm thick PEM-coated steel pin (triangles), sliding against glass at a normal stress of 250, 500, and 750 kPa; error bars reflect the maximum and minimum values obtained over three tests at each load level. Normal stresses are based on the pin diameter.

To study the friction behavior of PEM structures at varying normal loads, uncoated and 500 nm thick, (PAH 7.5/PAA 3.5) PEM-coated stainless steel pins were articulated against glass slides. For these tests, the PEM constructs were assembled with PAH as the last adsorbed polyelectrolyte, i.e., an additional "half bilayer" was employed. The average steady-state friction coefficients $\mu$ (ratio of tangential force to the normal force) over the course of three experiments at each load level are plotted as a function of the applied nominal normal stress in FIG. 4. The coefficient of friction for the uncoated steel-glass combination remained almost unchanged (0.09-0.15, see FIG. 4) over the range of stresses studied. On the other hand, when the pin was coated with PEMs, there was a wide range of friction forces observed at normal stresses of 250 and 500 kPa; the friction force was confined to a fairly narrow window at 750 kPa. There were no signs of wear particles, or rupture of the film on the pin surface at all these stress levels. At a stress of 750 kPa, the film is likely to be compressed to a reasonably uniform thickness when the pin is in contact with the glass slide. Hence there was a smaller variation in the friction forces between tests. Minimal orientation in the sliding direction on account of the entangled structure of the PEMs, film adhesion to the glass surface, some asperity penetration, and film deformation lead to a friction force that is higher than that exhibited by the bare steel pin. At stresses of 250 and 500 kPa, a lower degree of conformal contact between the pin and the glass may lead to non-homogeneities in the film thickness along the pin-glass interface, resulting in a larger range of friction coefficients depending on the conformation of the film in the dominant contact region.

When PEMs are coated onto the pin, the entire film experiences the same forces and deformations as the larger slider moves past it. Since no film or substrate wear was observed at these stresses, these friction coefficients reflect the characteristics of the native material pair; these are the "true" coefficients exhibited by the films (on steel) against glass Based on the adhesive component of friction force, Suh predicts decreasing coefficients with an increase in normal load for polymeric materials. See N. P. Suh, Tribophysics, Prentice-Hall, Inc., Englewood Cliffs, N.J., 1986, p. 241. This decrease in friction coefficient is related to the dependence of a polymer's shear strength on the applied hydrostatic pressure. An inkling of such a trend is observed in FIG. 4.

Tests were carried out to examine the possible effect of the polyelectrolyte functional groups on the friction force. When assembled at the (PAH 7.5/PAA 3.5) pH condition, the surface layer of the PEM structure is enriched with functional groups from the last adsorbed polyelectrolyte; the bulk structure is still interpenetrated. This surface enrichment is reflected by the observed contact angles. See S. S. Shiratori and M. F. Rubner *Macromolecules* 2000, 33, 4213-4219. At stress levels greater than or equal to 250 kPa, the friction coefficient was not affected by the choice of PAH or PAA as the uppermost layer. However, the friction coefficient was found to be smaller for PAH capped PEMs compared to PAA capped PEMs in experiments conducted at a 20 kPa stress level.

Dry State Wear Analysis of PEM-Coated Materials

Figure 5:
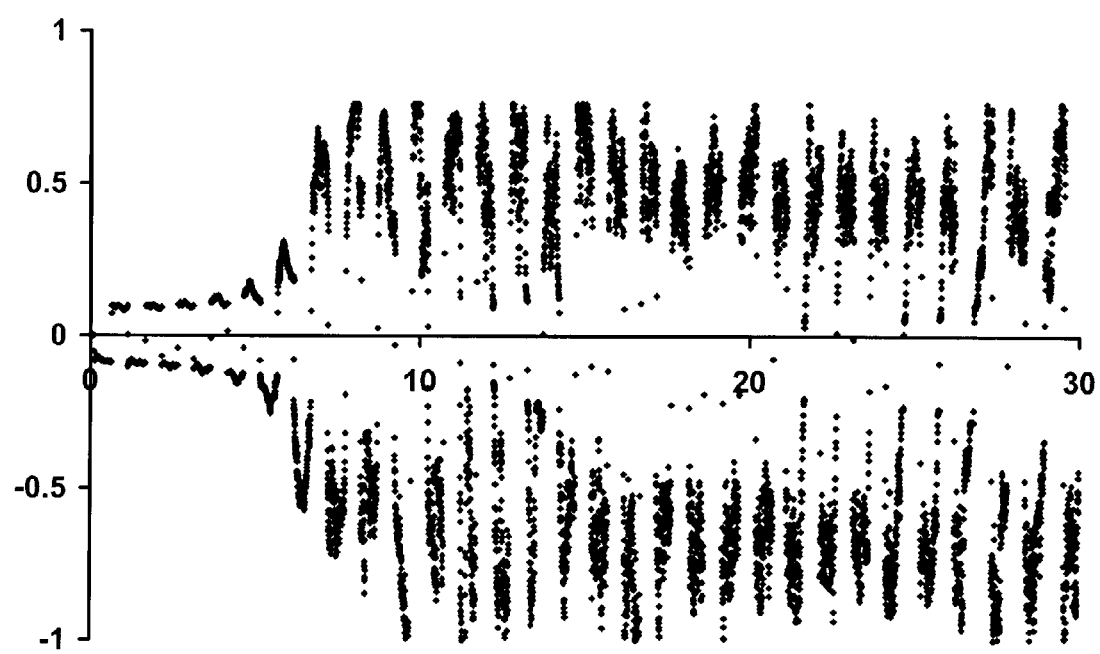
FIG. 5 depicts the friction profile for an uncoated tool steel pin slid against an uncoated stainless steel substrate. Normal stress 1 MPa based on diameter of pin.
Figure 6:
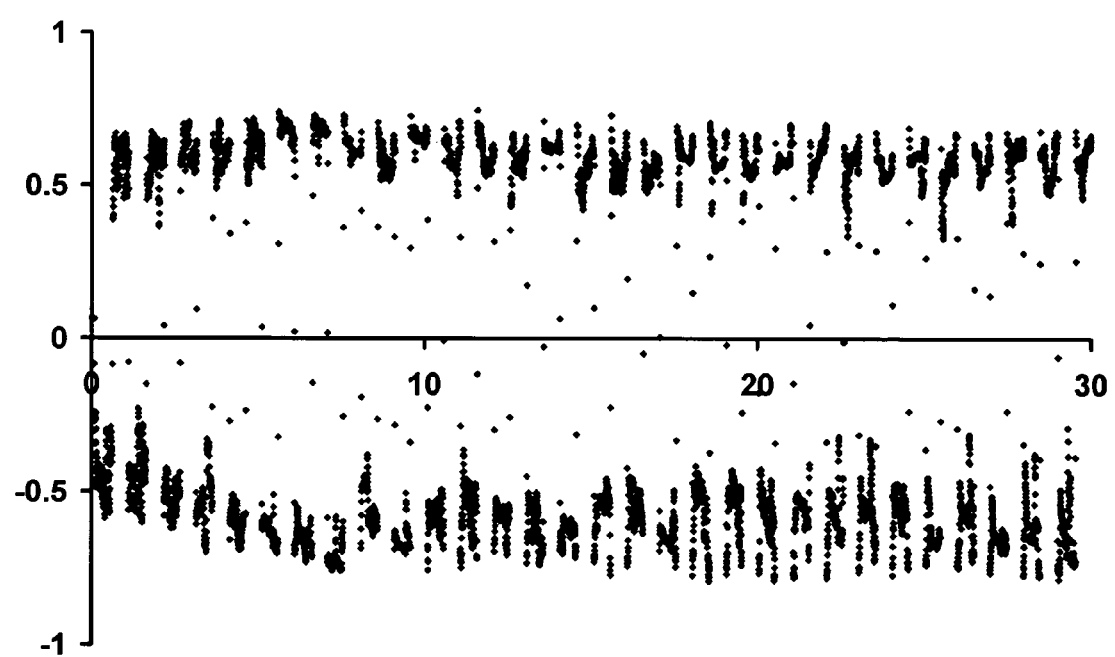
FIG. 6 depicts the friction profile for an uncoated tool steel pin sliding against a stainless steel slide coated with (PAH 7.5/PAA 3.5) 500 nm PEM assembly. Normal stress 1 MPa based on diameter of the pin.

The wear behavior of PEM-coated substrates was studied using (PAH 7.5/PAA 3.5) 500 nm PEM constructs; PAH was the last adsorbed polyelectrolyte. FIG. 5 depicts the friction coefficient profile for the case of an uncoated tool steel pin against an uncoated sliding stainless steel substrate over the 30-cycle duration of the test. Each curve in the graph represents the friction as the slider traverses the 3 mm path length; the change in sign indicates motion in the reverse direction. The evolution of the profile is similar to that described by Suh. See N. P. Suh, Tribophysics, Prentice-Hall, Inc., Englewood Cliffs, N.J., 1986, p. 73. Initially, the friction force is largely a consequence of plowing of the surface by asperities. The steep increase in friction force is attributed to the generation of wear particles. The increase in friction coefficient is thus a consequence of evolution of the interface, and the observed values of $\mu$ in this region are not representative of the frictional interaction between the native materials (in the absence of wear). FIG. 6 depicts the friction profile when the larger sliding steel substrate was coated with a 500 nm thick PEM assembly; the pin was uncoated. The frictional response in this configuration, unlike the case of the PEM-coated pin, is expected to be influenced by the film characteristics, by the interface between the film and the substrate, and perhaps by the substrate itself. It is evident that the evolutionary nature of the friction profile was suppressed by the PEMs. The coefficient of friction remained almost constant in the range 0.5-0.6 during the duration of this test.

Figure 7:
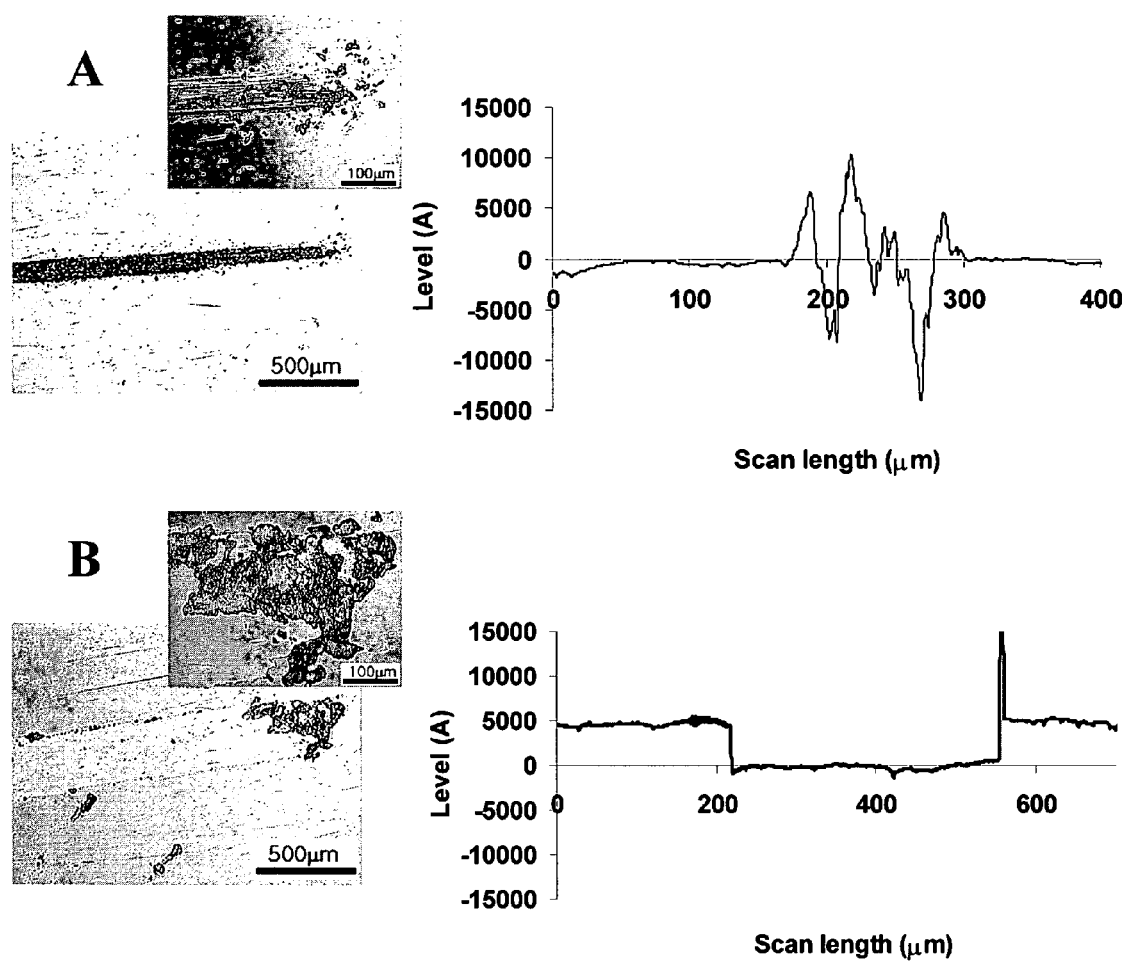
FIG. 7 depicts optical micrographs (insets depict higher magnification images of the ends of the wear track) and cross-sectional surface profiles for (a) Uncoated stainless steel slider, and (b) Steel slider coated with (PAH 7.5/PAA 3.5) 500 nm PEM construct. Counterface was uncoated tool steel pin, and normal stress was 1 MPa, in both cases.
Figure 8:
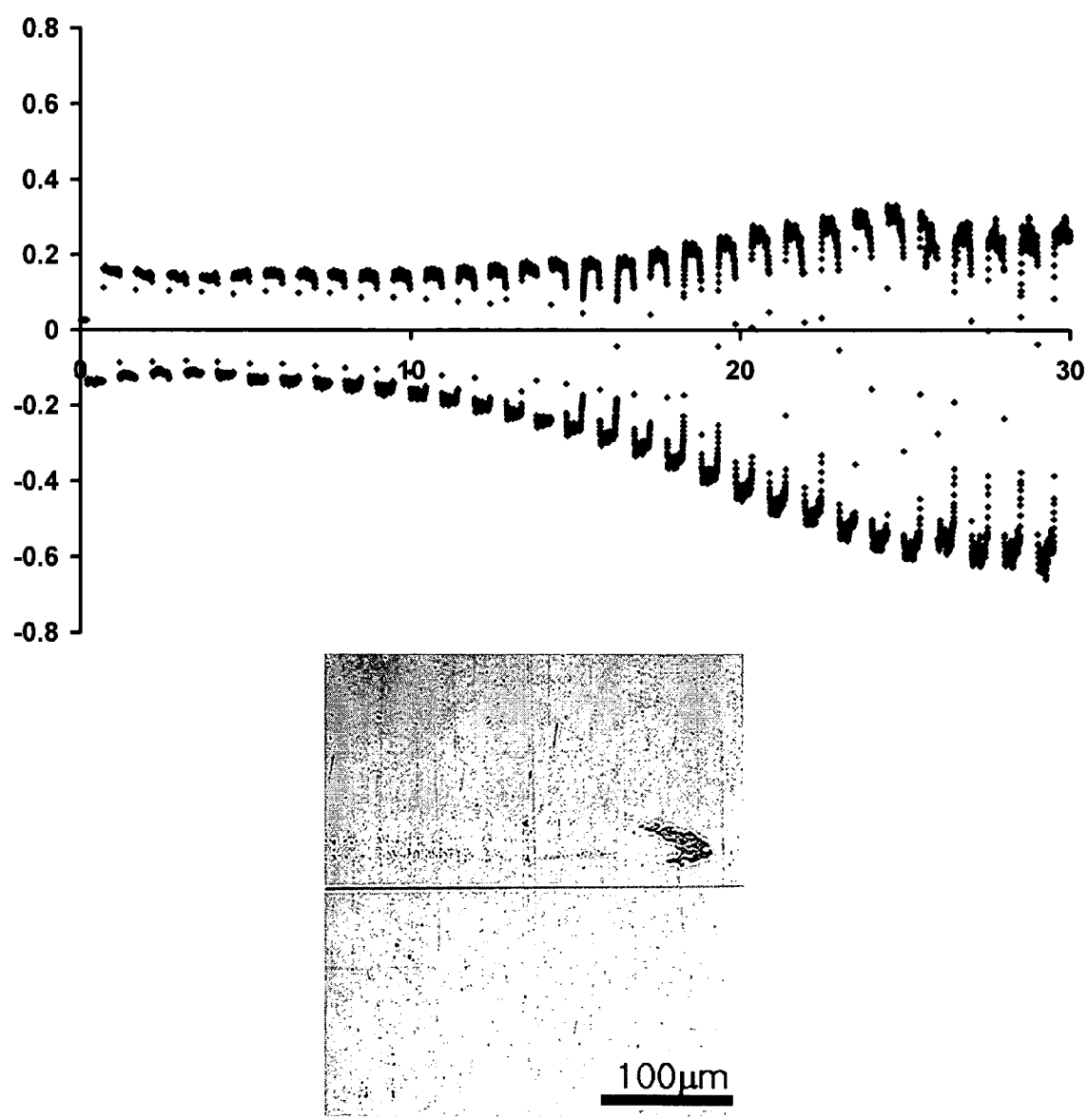
FIG. 8 depicts friction profiles and optical micrographs of the wear track for a (PAH 7.5/PAA 3.5) 500 nm PEM-coated stainless steel pin slid against bare stainless steel at a normal stress of 1 MPa.

To establish that an absence of evolution in the friction profile correlates with a virtual absence of substrate wear, the wear tracks, corresponding to the tests depicted in FIGS. 5 and 6, were analyzed using optical microscopy and cross-sectional surface profiling. The results are presented in FIG. 7. For the case of the bare steel substrate, a distinct wear track was observed; at higher magnifications, the wear particles, the principal cause of evolution of the friction profile, could also be seen. Examination of the cross-section of the wear track revealed pile-up of material alongside gouges up to 1.5 μm in depth. By contrast, there was essentially no wear of the metal surface when coated with the PEM. It was evident from the wear track profile that the 500 nm film had delaminated over the width of the track, but the underlying metal surface was protected; in rare cases, the film was observed to have retained its integrity over the wear track. PEM film fragments could be seen in the optical micrographs on the wear track, mostly at the ends, or occasionally on the surface of the pin; the deformation, adhesion, and dragging of these fragments at the interface results in the high observed friction forces. The mechanism of wear prevention evidently lies primarily in the presence of PEM fragments between the pin and the slider because the film is usually removed from parts of the track within the first few cycles of the test. There was no evidence of the metal debris or deep gouges that were apparent in the wear track for the uncoated metal-on-metal system. The wear of a bare steel substrate over the 30-cycle duration of the test was also avoided when the pin was film-coated with a 500 nm PEM. The evolution in the friction profile, depicted in FIG. 8, is attributed to limited fragmentation of the film during the test, and not due to wear particles.

Several interesting observations can be made from the summary of the wear experiments in Table 1. All the 500 nm PEM constructs (Table 1, line 3-5) prevented substrate wear. In the early stages of an experiment, the uncoated metal-on-metal pair has a low friction coefficient of 0.1; however, the generation of wear debris rapidly elevates this value (FIG. 5). A relatively thick PEM coating (500 nm) elevates the value of $\mu$ substantially to approximately 0.6 (Table 1, line 3) but this value includes a mechanism of dragging and deforming PEM film-debris at the pin-slider interface. Thinner PEM films (compare Table 1, line 6, 7 and 8) show promise for simultaneously minimizing the friction coefficient and the wear of the substrate. A reduction in thickness compromises the wear-reducing efficacy of the PEM fragments (Table 1, line 7). This observation is also demonstrated by a 1 bilayer PEM assembly, approximately 9-15 nm thick on steel (for reference, a 20 nm film consists of 3 bilayers, while 8 bilayers are needed for a 70-80 nm thick film assembled at the (PAH 7.5/PAA 3.5) combination). Wear reduction was only occasionally observed for this very thin PEM; a low friction coefficient of 0.2 resulted in the absence of substrate wear. When the PEM is placed only on the pin (Table 1, line 4) the production of PEM film debris is almost negligible and the low value of the steel-steel friction coefficient is approached in the initial portion of the experiment. For the same thickness, PEMs on the larger surface offer more material for wear prevention.

TABLE 1

Summary of experiments designed to elucidate wear behavior of PEM constructs on different substrates (dry state)

| | PIN | Slider | (PAH 7.5/PAA 3.5) PEM Characteristics | Normal Stress[b] (MPa) | Evolution in Friction Profile[c]? | Wear of Slider? | $\mu$ (or range) |
|---|---|---|---|---|---|---|---|
| 1 | Tool steel | SS[a] | — | 1 | Yes | Yes | 0.09-0.57 |
| 2 | SS | SS | — | 1 | Yes | Yes | 0.13-0.34 |
| 3 | Tool steel | SS | On slider, 500 nm | 1 | No | No | 0.58 |
| 4 | SS | SS | On pin, 500 nm | 1 | Yes | No | 0.14-0.35 |
| 5 | SS | SS | On slider and pin, 500 nm | 1 | No | No | 0.81 |
| 6 | Tool steel | Si <111> | — | 4 | Yes | Yes | 0.1-0.58 |
| 7 | Tool steel | Si <111> | On slider, 20 nm | 4 | No[d] | No[d] | 0.23 |
| 8 | Tool steel | Si <111> | On slider, 80 nm | 4 | No | No | 0.49 |

Figure 9:
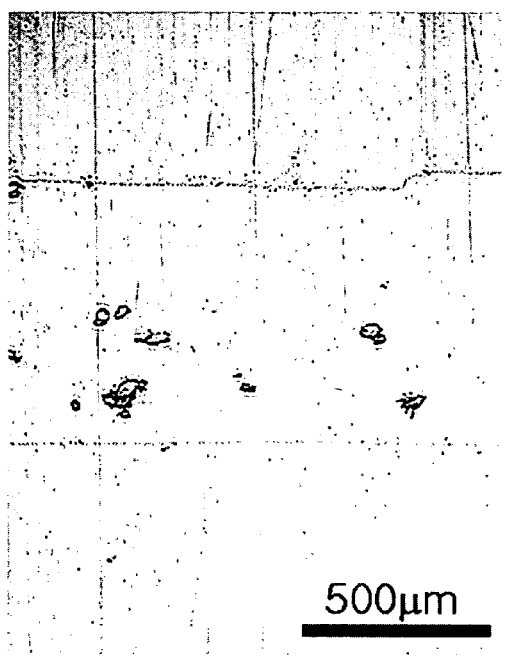
FIG. 9 depicts optical micrographs of the wear track when a PEM-coated steel pin was articulated against a PEM-coated steel slide at a normal stress of 1 MPa; both PEMs were assembled at the (PAH 7.5/PAA 3.5) combination and were 500 nm thick.
Figure 9:
Figure 10:
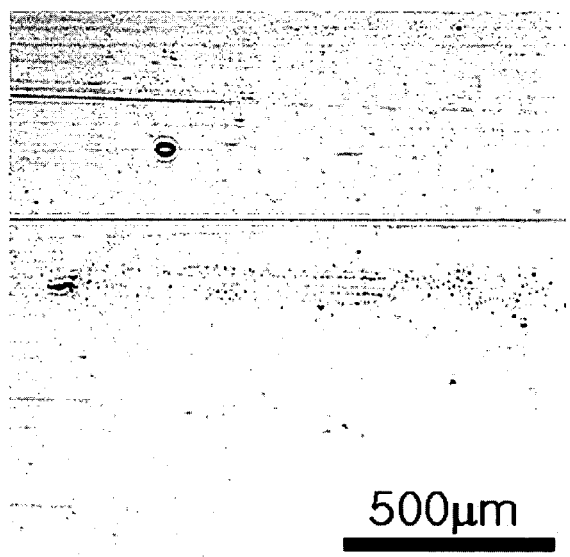
FIG. 10 depicts optical micrographs of the test region on the bare steel slider and the steel pin (used for the test depicted in FIG. 9) after 30 cycles of reciprocating motion at a normal stress of 1 MPa. There is negligible wear of the steel slider; PEM fragments from the slider in FIG. 9 can be seen on the PEM-coated pin.
Figure 10:
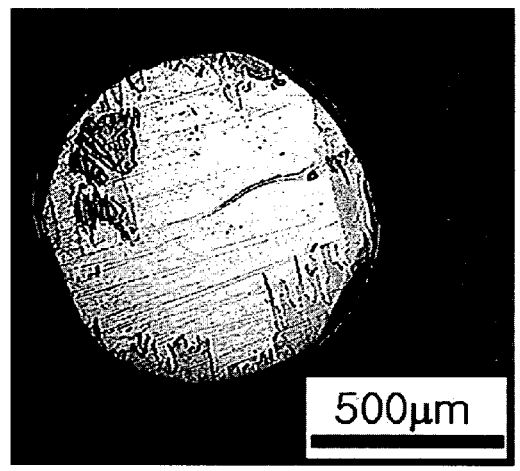

[a]Stainless steel type 316
[b]Based on the diameter of the pin
[c]Over the duration of a 30-cycle test, unless otherwise specified
[d]After 20 cycles, however, wear of the silicon substrate was observed Further evidence for the important role of PEM fragments in wear reduction is shown in FIGS. 9 and 10. FIG. 9 presents optical micrographs of a wear-free track on the slider for the case in which both the stationary steel pin and the sliding steel substrate were coated with 500 nm thick PEMs. At a normal stress of 1 MPa, no wear of the steel substrate was observed; the friction coefficient remained at a steady value of approximately 0.8 during the length of the test (Table 1, line 5). The PEM on the steel slider was removed along the 3 mm path length. When the same pin was subsequently tested against an uncoated stainless steel slide, a profile similar to that depicted in FIG. 8 was obtained. The original film on the pin, in conjunction with some fragments transferred from the coated original steel slide, was successful in preventing wear of the substrate over 30 cycles. Optical micrographs of the test region on the steel slide and the pin, at the end of the test, are presented in FIG. 10. This configuration is recommended for make-and-break type of contact situations, in which contact may not always be reestablished at the point of severance, i.e., where the advantageous PEM-fragments lie on the wear track. The PEM constructs on the pin will, however, still be available to prevent substrate wear during the second run.

Of course, a trade-off exists between lowering the friction coefficient and avoiding early initiation of substrate wear when the slider is PEM-coated. Films on the slider must have a certain minimum thickness to supply the desirable wear-reducing properties. Slightly higher thicknesses are required for steel substrates compared to silicon, owing to the higher associated surface roughness.

Figure 11:
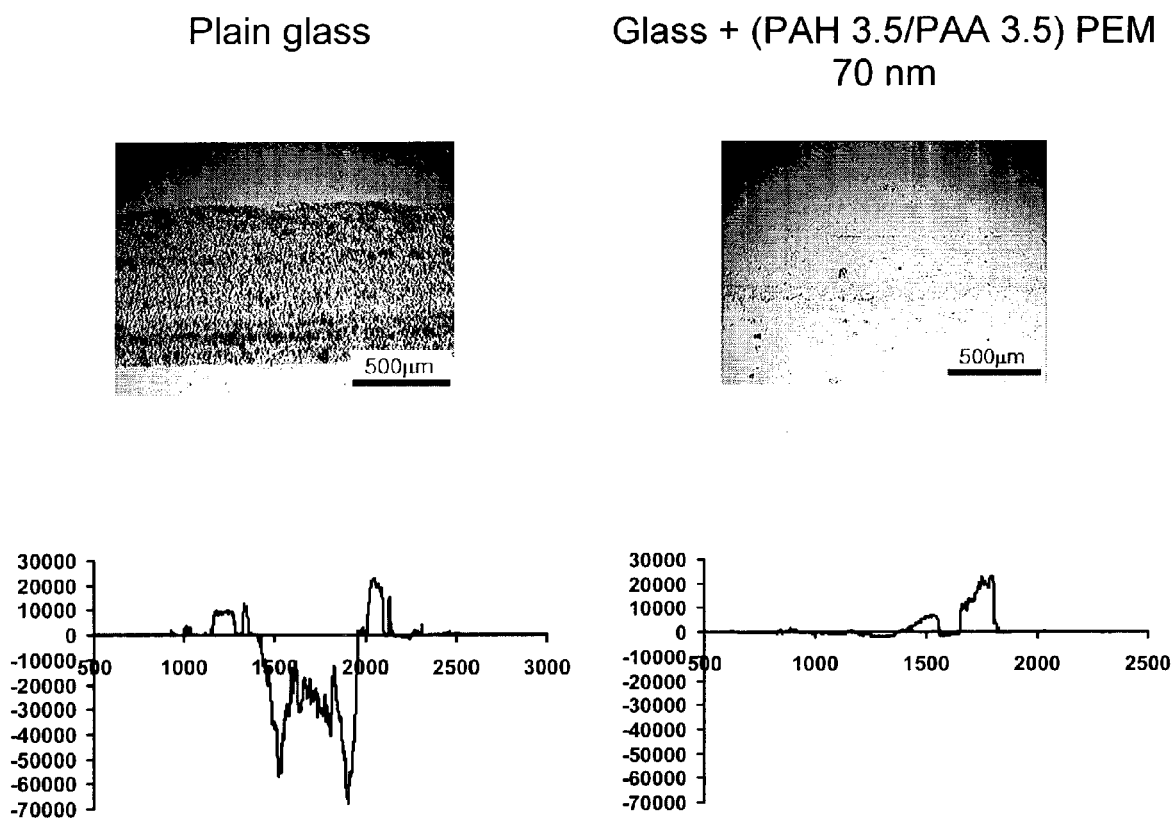
FIG. 11 depicts optical micrographs and cross-sectional surface profiles of wear tracks after macroscale pin-on-disk tests (2000 cycles).

To examine the efficacy of the films with respect to wear reduction over a larger number of cycles and normal pressures, tests were carried out on a macroscale pin-on-disk wear tester. Assuming elastic contact between the steel pin and the glass substrate, the maximum contact stress for the 3.5 N load was calculated to be 450 MPa using Hertzian analysis. Optical micrographs and surface profiles of the wear tracks after 2000 cycles of reciprocating motion, on coated and uncoated glass substrates, are presented in FIG. 11. In the case of the uncoated glass slide, steel deposition from the pin onto the wear track was observed within the first few cycles. Cross-sectional profiles indicated wear track depths up to 7 μm. Conversely, for glass coated with a (PAH 3.5/PAA 3.5) 70 nm film, no steel deposition was seen, and a clean wear track was obtained at the end of 2000 cycles. The wear-track profile indicated film removal over the width of the wear track, but absence of substrate wear.

At thicknesses of about 500 nm, the pH values of the assembly solutions do not play a significant role in the wear reducing power of PEM fragments. At lower thicknesses, however, the differences in the degrees of ionic-crosslinking in the (PAH 7.5/PAA 3.5) and (PAH 3.5/PAA 3.5) constructs could have an effect on the load bearing capacity of these films. See S. S. Shiratori and M. F. Rubner Macromolecules 2000, 33, 4213-4219. Nanoindentation is currently being used to characterize the mechanical behavior of PEMs assembled at varying pH combinations.

At stresses causing wear of unprotected silicon, 20-80 nm thick PEMs exhibited low friction forces coupled with an absence of substrate wear (Table 1, lines 6,7, and 8). The friction coefficients of PEM-coated substrates, however, are higher than the value of 0.1 exhibited by the bare silicon substrate, prior to the onset of wear. Adhesion of the hydrophilic films to the counterface, some asperity penetration, and resistance to orientation in the direction of sliding are the likely causes for the higher friction forces. Strategies that are being explored in an effort to reduce the friction coefficients include surface capping of these films with mechanically hard outer layers, block co-polymers, and easy to orient layers. In addition, introduction of metallic nanoclusters, metal oxide nanoclusters, metal sulfide nanoclusters, carbon nanotubes, graphitic and clay nano-platelets into the PEM structures are being investigated to enhance the performance of the film.

Wear Analysis of PEM-Coated Materials in a Liquid Medium

PAH-PAA PEMs are being investigated for wear reduction in orthopedic implants; wear debris is known to induce bone resorption in a normal implant leading to its loosening. See E. Ingham and J. Fisher, Biological reactions to wear debris in total joint replacement, Proc. Instn. Mech. Engrs. Part H-Journal of Engineering in Medicine, 214(H1) (2000) 21-37. Surface modification of the commonly used metal-on-plastic or metal-on-metal configurations to reduce the wear rates offers a potential solution to this problem without compromising the bulk mechanical properties. See M. R. Widmer, M. Heuberger, J. Voros and N. D. Spencer *Tribology Letters* 2001, 10, 111-116. Bovine calf serum is routinely used as the lubricant to simulate the presence of joint synovial fluid. The lubricant solution normally contains EDTA to retard protein precipitate formation (See V. K. Polineni, A. Wang, A. Essner, C. Stark and J. H. Dumbleton, Effect of lubricant protein concentration on the wear of UHMWPE acetabular cups against cobalt-chrome and alumina femoral heads, 23rd Annual Meeting of the Society for Biomaterials, New Orleans, La., U.S.A., 1997); also, sodium azide serves as an antibacterial agent. The pH of this solution is at physiological levels, i.e., around 7. In addition to inorganic salts, calf serum primarily contains two proteins: albumin and γ-globulin. It is known that the PEM structure is responsive to the ionic strength and pH of the surrounding medium. See T. C. Wang, R. E. Cohen and M. F. Rubner *Adv. Mater.* 2002, 14, 1534-1537. Hence careful consideration needs to be given to the choice of polyelectrolyte assembly pH when calf serum is used as a lubricant. PEMs (PAH 7.5/PAA 3.5) used in the present invention exhibit very little structural rearrangement at physiological pH conditions; the uniformity and thickness of these films remains essentially unaltered. Thermally induced crosslinking at 130° C. for 3 hours further stabilizes these films. See J. J. Harris, P. M. DeRose and M. L. Bruening *J. Am. Chem. Soc.* 1999, 121, 1978-1979.

Table 2 outlines the results indicating the wear behavior of PEM-coated stainless steel in the presence of water. A (PAH 3.5/PAA 3.5) 70 nm construct was assembled on the steel slider; the tool steel pin was uncoated. The pin-slider interface was submerged in water. Analogous to the dry state tests, PEM fragments inhibited wear particle generation, and hence evolution of the friction curve over the 30-cycle duration of the test. Again, adhesion to the counterface and dragging of the hydrated fragments at the interface contributed to a friction force that was higher than the control experiment.

TABLE 2

Wear Behavior of PEM-coated Steel Substrates in Water

| PIN | Slider | (PAH 3.5/PAA 3.5) PEM Characteristics | Normal Stress[b] (MPa) | Evolution in Friction Profile[c]? | Wear of Slider? | μ (or range) |
|---|---|---|---|---|---|---|
| 1 Tool steel | SS[a] | — | 1 | Yes | Yes | 0.12-0.32 |
| 2 Tool steel | SS | On slider, 70 nm | 1 | No | No | 0.50 |

Figure 12:
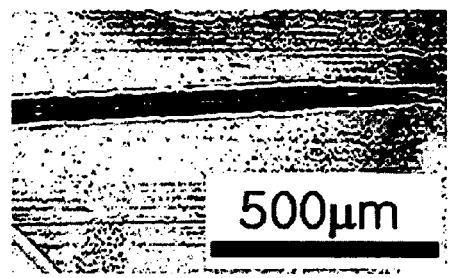
FIG. 12 depicts optical micrographs and surface profiles of wear tracks on a plain stainless steel slide, and steel coated with 100 nm PEM. Tests conducted in calf serum lubricant at a normal stress of 2 MPa. Original metal surface is at level zero.
Figure 12:
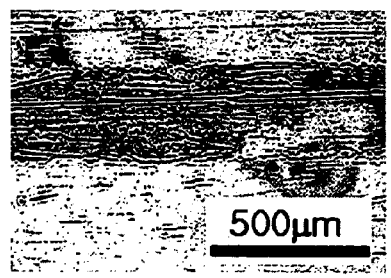
Figure 12:
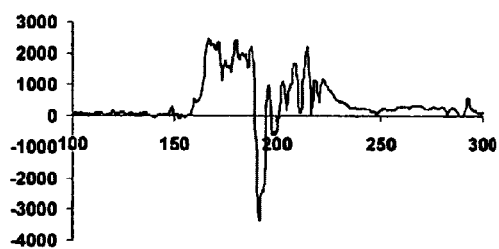
Figure 12:
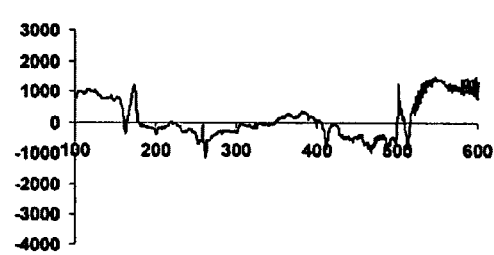

[e]Stainless steel type 316
[f]Based on the diameter of the pin
[g]Over the duration of a 30-cycle test Tribological tests on the crosslinked films in bovine calf serum were conducted using the biaxial apparatus; a tool steel pin was made to articulate against a PEM-coated stainless steel slide at a normal stress of 2 MPa. Physiological stress levels in the human hip joint are in the 3-6 MPa range. See A. Wang, A. Essner, V. K. Polineni, D. C. Sun, C. Stark and J. H. Dumbleton, Lubrication and wear of ultra-high molecular weight polyethylene in total joint replacements, in: I. M. Hutchings (Ed.), New Directions in Tribology, Mechanical Engineering Publications Limited, Bury St Edmunds, UK, 443-458, 1997. FIG. 12 depicts wear track analysis for the PEM-coated and uncoated steel slides, submerged in the calf serum-containing lubricant, after 30 cycles of reciprocating motion; both substrates were immersed in the lubricant for 24 hours prior to testing. The serum served as a lubricant for the uncoated steel slide by reducing the wear track depth to approximately 0.3 μm at a normal stress of 2 MPa, compared to 1.5 μm at 1 MPa stress when water was used as the surrounding medium. The friction profile exhibited minimal evolution with an average friction coefficient of about 0.3. When the steel slide was coated with a 100 nm crosslinked PEM, no wear of the substrate was observed. Surface profiles pointed to the role of PEM fragments in wear reduction. The friction coefficient remained at 0.3, close to that of the uncoated substrate. These tests suggest the potential merit of PEM-induced surface modification for metallic substrates when bovine calf serum is used as the lubricant.

Friction Analysis of PEM-Coated Materials

Figure 13:
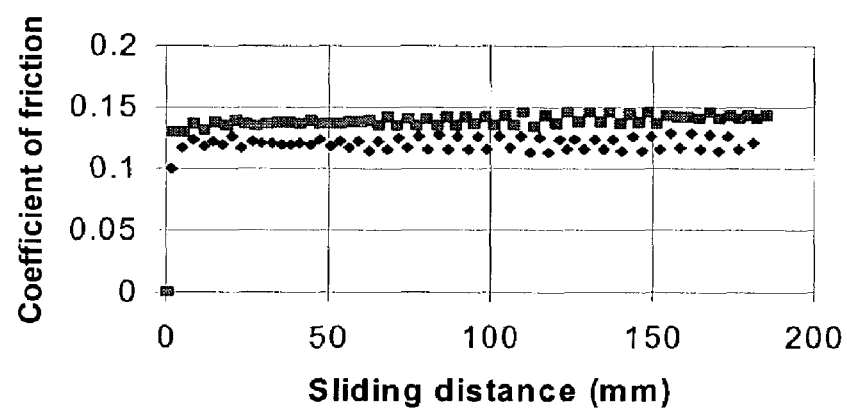
FIG. 13 depicts coefficients of friction for a glass substrate and a PEM (PAA/PAH) coated substrate.
Figure 13:
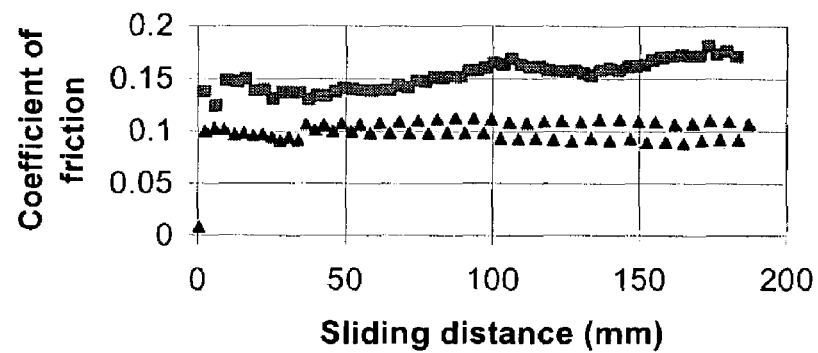
Figure 14:
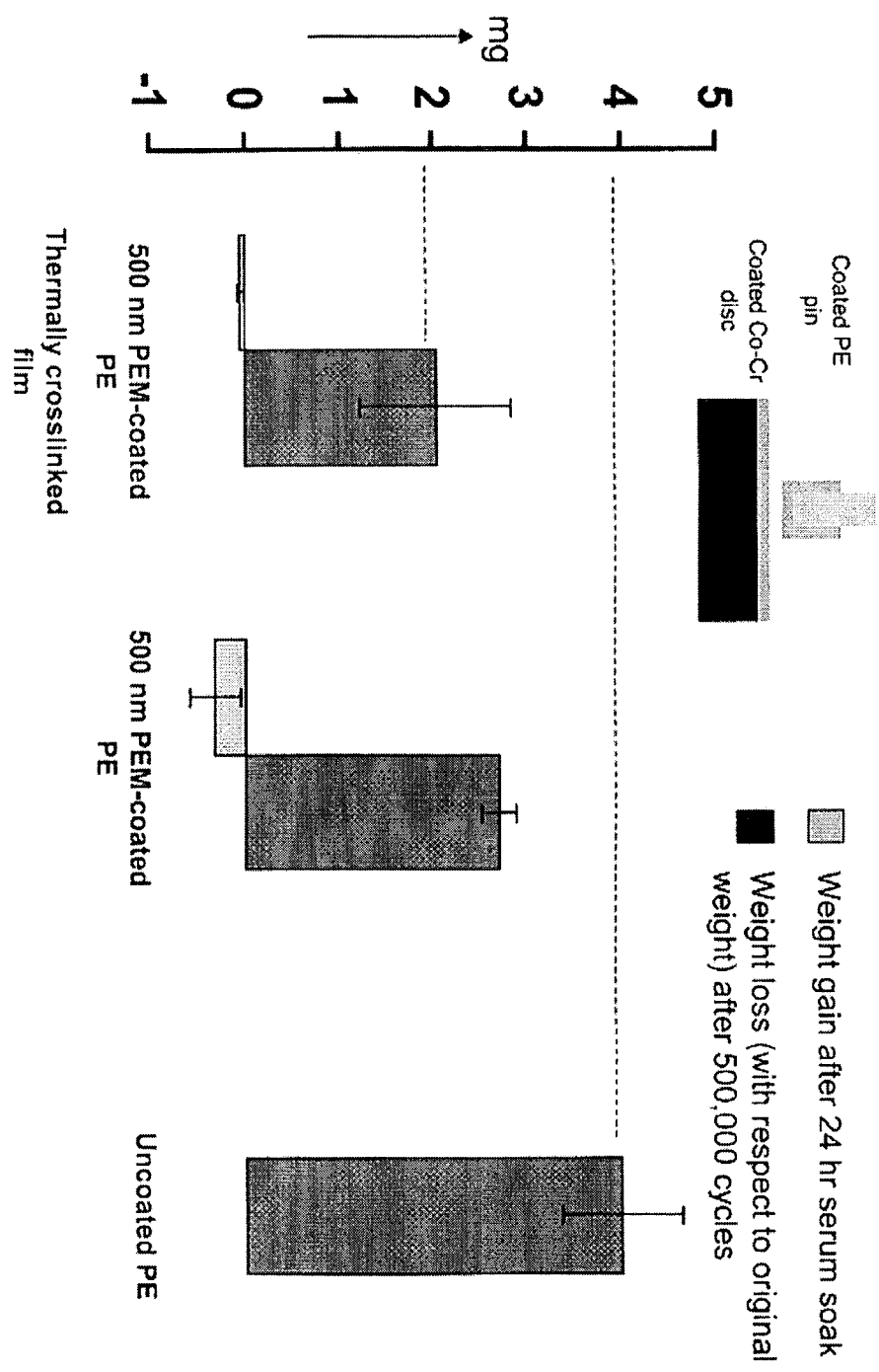
FIG. 14 depicts the results of wear tests of PEM coated substrates and Co—Cr disks articulating in a pin-on-disk tester over 50000 cycles in the presence of bovine calf serum. Weight changes are for UHMWPE pins.

The evolution of the friction coefficient (at 20 kPa) with sliding distance is depicted in FIG. 13 for plain glass, and glass coated with a 70 nm thick PEM at a. For this film, assembled at a pH of 3.5 for both polyelectrolytes, there is a concentration of both the cationic and anionic groups at the surface. The film did not produce a noticeable change in the coefficient of friction. Differences in the local adhesion of the PEMs may contribute to the variability in friction for the two specimens, within certain bounds. When the pH of PAH (polycation) is 7.5 and that of PAA (polyanion) is 3.5, the surface of the PEM is composed of functional groups of the last adsorbed polyelectrolyte. In this case, PAA topped films exhibited a higher average friction coefficient of 0.27 compared to films having PAH as the last adsorbed polyelectrolyte (friction coefficient of 0.09 over the 180 mm sliding distance).

For the case of ultra-high molecular weight polyethylene (UHMWPE), the results are tabulated in Table 3. A stress of 4 MPa was used since it simulates physiological loading conditions for the hip. Average values of coefficient of friction, over the 180 mm sliding distance were calculated without considering the initial transient response. It is obvious that the films cause an increase in tangential force compared to the plain polymer. Interestingly, PAH topped films exhibited lower friction compared to their PAA topped counter parts.

TABLE 3

Average values of friction coefficients for UHMWPE coated with PEMs

| Substrate | Film Thickness (nm) | Friction Coefficient |
|---|---|---|
| UHMWPE | | 0.05 |
| UHMWPE + PEM (PAH 3.5'/PAA 3.5) | 62 | 0.14 |
| UHMWPE + PEM (PAH 7.5/PAA 3.5) PAH on top | 82 | 0.15 |
| UHMWPE + PEM (PAH 7.5/PAA 3.5) PAA on top | 102 | 0.18 |

Wear Reduction in Orthopedic Implants

Surface engineering, via thin organic films offers the potential for wear reduction in systems as diverse as total joint replacement prostheses and microelectromechanical systems (MEMS). Orthopedic implants, with metal-on-plastic configurations, have employed an ultra-high molecular weight polyethylene (UHMWPE) bearing surface for almost four decades. The life of the implant is limited by the wear of UHMWPE; the wear debris induces bone resorption through a biological reaction, causing implant loosening, and necessitating a revision surgery. Radiation-induced crosslinking of the polymer has been shown to drastically reduce the wear rate of the polymer. See Gomoll, A.; Bellare, A.; IWanich, T. in *Deformation, Yield, and Fracture of Polymers: 11th International Conference* 254 (2000). But a reduction in wear is accompanied by a loss of ultimate mechanical properties of UHMWPE. Surface modification could lower the wear rates without compromising the bulk mechanical properties. Widmer an co-workers modified the surface hydrophilicity of UHMWPE through oxygen-plasma treatment; improved boundary lubrication, through protein adsorption, was hypothesized to reduce wear rates. See R. M. Widmer et. al. *Tribology Letters*, 2001, 10, 111-116. The authors reported a decrease in dynamic friction, and stiction, following the plasma treatment. However, the effect of the plasma treatment was short-lived. In addition, no wear experiments were carried out to establish the effect of change in surface properties on wear mechanisms.

There has been a resurgence of interest in metal-on-metal configurations for orthopedic implants because of the problems associated with wear of UHMWPE. Metal-on-metal pairings have been shown to be associated with wear volumes 40-100 times lower than a metal-UHMWPE pairing.

See Ingham, E.; Fisher, J. in *Proc. Instn. Mech. Engrs.* 2000, 21-37. However, since these metallic-wear particles are smaller than those of UHMWPE, a larger number of particles are produced for the same mass of wear debris. In addition to inducing implant loosening, these particles are believed to undergo electrochemical corrosion leading to high ion serum concentrations. Another concern is the dissemination of these metal particles to other parts of the body, where they would be responsible for long-term toxic effects, including carcinogenicity. Surface modification of the metal surface via thin films could circumvent the wear, and subsequent corrosion problems.

Polyelectrolyte Multilayers

A polyelectrolyte multilayer used according to the methods of the present invention may comprise any combination of a wide range of individual polyelectrolytes. Table 4 depicts various polyelectrolytes that may be utilized according to the methods of the present invention. It is understood by one of ordinary skill in the art that polymers containing charged functional groups have a counterion such that the overall net charge is neutral. For example, each ammonium ion functional group of PAH has a negatively charged counter ion, such as a halogen, carboxylate, sulfonate, ect. In certain embodiments, the positive charge of the ammonium ion functional group of PAH is balanced by the negative charge of a chloride anion. Additional representative examples of polyelectroytes that can be used to prepare PEM are τ-carrageenan (CAG), poly[1-[4-(3-carboxy-4-hydroxy phenyl-azo)benzenesulfonamido]-1,2-ethanediyl, sodium salt (PAZO), polyvinylsulfate (PVS), poly(3-sulfopropylmethacrylate) (PSPM), poly(acrylamido-2-methyl-propanesulfonate), poly (3-sulfopropylitaconate) (PSPI), polyester, poly(etherketone), poly(ethersulfone), poly(L-glutamic acid) PGA, exfoliated suspensions of lamellar metal disulfides, Nafion®, Chondroitin sulfate, Dextran sulfate, Poly(γ-benzyl-glutamate), DuPont VF2/PSEPVE, Poly(vinyl alcohol) PVA, Poly (2-ethyl-2-oxazoline) OX, Human serum albumin (HSA), Poly(2-acrylamido-2-methyl-1,propanesulfonic acid) PAMPS, poly(diallyldimethylammonium chloride) (PDADMA), poly(ethyleneimine) (PEI), poly(4-vinylpyridine) (P4VP), β-cyclodextrin (chloride salt), ionenes, poly (L-lysine) PLL, quaternized dimethylaminoethyl methacrylate (AMA), chitosan, avidin, heparin, and charged nanoobjects—colloidal dispersions of charged silica, metal oxides, semiconductor, nanoparticles, fullerenes, montmorillonite clay, charged latex spheres, graphite, or carbon nanotubes. A more thorough review of polyelectrolytes used in the preparation of multilayer films can be found in the article Bertrand, P.; Jonas, A.; Laschewsky, A.; Legras, R. *Macromol. Rapid Commun.* 2000, 21, 319-348. PEMs can be prepared according to the method first reported by Decher, involving the layer-by-layer adsorption of oppositely charged polyelectrolytes, leading to structures whose architectures are controlled by the choice of processing conditions and the polyelectrolyte pair. See G. Decher *Science* 1997, 277, 1232-1237. Structures of the repeat units of two polyelectrolytes used in the present invention, poly (acrylic acid) (PAA) and poly(allylamine hydrochloride) (PAH), are depicted in FIG. 1. It is noteworthy that PEMs can also be prepared relying on hydrogen bonding interactions. In these examples, preferred polyelectrolytes are poly (4-vinylpyridine), PAA, polyaniline, poly(vinylpyrrolidone), poly(acrylamide), poly(ethylene oxide).

Figure 2:
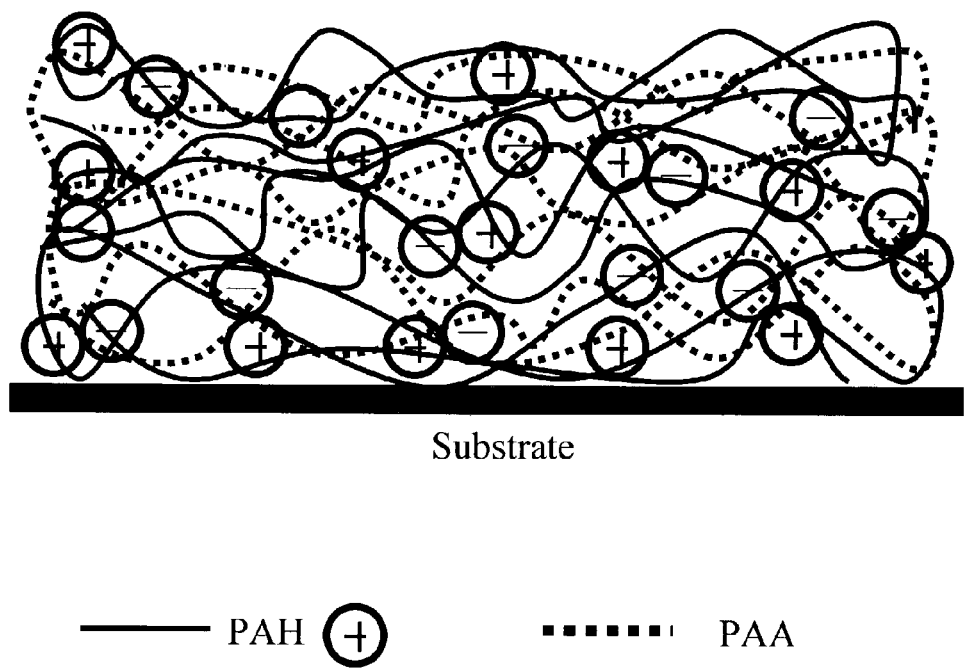
FIG. 2 depicts the interpenetrated bulk structure of a PAA/PAH PEM. Solid lines represent PAH, and dashed lines represent PAA.

Rubner and co-workers have demonstrated that by changing the pH of polyelectrolyte solutions, relative to their pKa values, the extent of ionization of the functional groups, and hence the ionic-crosslink density of the PAH-PAA pair, can be controlled. See D. Yoo, S. S. Shiratori and M. F. Rubner *Macromolecules* 1998, 31, 4309-4318 and S. S. Shiratori and M. F. Rubner *Macromolecules* 2000, 33, 4213-4219. This facilitates tuning of PEM architectures with respect to film thickness, interfacial roughness, and nature of functional groups at the surface (i.e., contact angle). Although assembled using a layer-by-layer technique, neutron and x-ray reflectometry, and a less direct method employing the introduction of metallic nanoclusters have been used to show that the internal structure of these films consists of a relatively interpenetrated network. See S. Joly, R. Kane, L. Radzilowski, T. Wang, A. Wu, R. E. Cohen, E. L. Thomas and M. F. Rubner *Langmuir* 2000, 16, 1354-1359. A schematic of the PEM structure is illustrated in FIG. 2.

In addition to tunable architectures, PAH-PAA PEMs provide the advantage of being easy to fabricate. Assembly is aqueous based, and proceeds at ambient conditions. The entire layer-by-layer assembly process can be automated. A distinct advantage of these films over other surface modification techniques, like self-assembled monolayers, is that PEMs can be assembled on a wide variety of substrates with little or no pretreatment. Strongly adhering films, resistant to scotch-tape peel tests (P. C. Hidber, W. Helbig, E. Kim and G. M. Whitesides, *Langmuir* 1996, 12, 1375-1380), have been formed on glass, polystyrene, polyethylene, silicon, and stainless steel. See J. A. Hiller, J. D. Mendelsohn and M. F. Rubner *Nature Materials* 2002, 1, 59-63. Being conformal, substrates of complex shapes can be coated successfully, with uniformity over large areas.

Another advantage of using PEMs is that numerous other materials and polymers may be incorporated into the multilayer. In certain embodiments a metallic nanocluster, such as a silver nanocluster, $MoS_2$ nanocluster, or $WS_2$ nanocluster, may be incorporated in the multilayer. See M. F. Rubner et. al. *Langmuir* 2000, 16, 1354. Examples of polymer may include but are not limited to poly(ethylene oxide), poly (vinyl alcohol), poly(ethylene imine), poly(diallyldimethylammonium chloride), chitosan, glycosaminoglycans, polylysine, poly(glutamic acid), poly(aspartic acid), alginate, RNA, DNA and enzymes.

TABLE 4

Various polyelectrolytes comprised by multilayers transferred according to the methods of the present invention.

| Polymer Name | Polymer Abbreviation | Polymer Structure | Charge/pH dependent or indendent |
|---|---|---|---|
| Polyacrylic acid | PAA | $\left[ CH_2-\underset{COO^-}{\overset{H}{C}} \right]_n$ | Anionic/ pH dependent |
| Polyallylamine hydrochloride | PAH | $\left[ CH_2-\underset{\underset{NH_3^+}{CH_2}}{\overset{H}{C}} \right]_n$ | Cationic/ pH dependent |

TABLE 4-continued

Various polyelectrolytes comprised by multilayers transferred according to the methods of the present invention.

| Polymer Name | Polymer Abbreviation | Polymer Structure | Charge/pH dependent or indendent |
|---|---|---|---|
| Polyacrylamide | PAAm | —[CH₂—CH(C(=O)NH₂)]ₙ— | Neutral |
| Polymethacrylic acid | PMA | —[CH₂—C(CH₃)(COO⁻)]ₙ— | Anionic/ pH dependent |
| Polystyrene sulfonate | SPS | —[CH₂—CH(C₆H₄SO₃⁻)]ₙ— | Anionic/ pH independent |
| Polydiallyldimethyl-ammonium chloride | PDAC | (pyrrolidinium ring with N⁺(CH₃)₂ Cl⁻) | Cationic/ pH independent |

Substrate

The mild conditions employed for binding the multilayer film to the substrate make this process amenable to a wide variety of substrate materials. The substrate may be a homogeneous or composite material. In general, the substrate may include plastic, metal, wood, glass, fiberglass, fabric, semiconductor, and textiles. Representative examples include: cotton, wool, silk, jute, linen, rayon, acetate, polyesters, polyethyleneterephthalate, polyamides, nylon, acrylics, olefins, aramids, azlons, glasses, fiberglass, modacrylics, novoloids, nytrils, rayons, sarans, vinyon, films, natural leathers, split hydes, synthetic leathers, vinyl, urethane, polyurethane, polyurethane films, polyethylene, ultra-high molecular weight polyethylene, polymeric silicon layers, poly(dimethyl siloxane), single crystal silicon, polycrystalline silicon, silicon oxide, silicon nitride, filtration membranes, polysulfones, polyimides, nitrocellulose, cellulose acetate, cellulose, and regenerated cellulose, and combinations thereof. In certain embodiments, the substrate is a silicon-based material. In some cases, it is advantageous to modify the surface of the substrate to promote binding of the multilayer film to the substrate. In order to make interaction forces between multilayers and substrates stronger, functionalities can be introduced onto substrate surfaces by various techniques such as plasma treatment.

PEM-Coated Medical Devices of the Invention

One aspect of the present invention relates to an implantable medical device comprising a surface coated with a polyelectrolyte multilayer, wherein said surface is glass, metal, plastic, polymer, or fiberglass.

In certain embodiments, the present invention relates to the aforementioned device, wherein said polyelectrolyte multilayer comprises a linear or branched poly(acrylic acid), poly(allylamine hydrochloride), poly(ethylene imine), poly (diallyldimethylammonium chloride), sulfonated polystyrene, or poly(2-acrylamido-2-methyl-1-propane-sulfonic acid).

In certain embodiments, the present invention relates to the aforementioned device, wherein said polyelectrolyte multilayer comprises a linear or branched poly(acrylic acid) or poly(allylamine hydrochloride).

In certain embodiments, the present invention relates to the aforementioned device, wherein said polyelectrolyte multilayer comprises linear or branched poly(acrylic acid) and poly(allylamine hydrochloride).

In certain embodiments, the present invention relates to the aforementioned device, wherein said surface is metal, plastic, or polymer.

In certain embodiments, the present invention relates to the aforementioned device, wherein said surface is metal.

In certain embodiments, the present invention relates to the aforementioned device, wherein said surface is stainless steel.

In certain embodiments, the present invention relates to the aforementioned device, wherein said surface is plastic.

In certain embodiments, the present invention relates to the aforementioned device, wherein said surface is ultra-high molecular weight polyethylene.

In certain embodiments, the present invention relates to the aforementioned device, wherein said surface is metal and said polyelectrolyte multilayer comprises poly(acrylic acid).

In certain embodiments, the present invention relates to the aforementioned device, wherein said polyelectrolyte multilayer is less than about 700 nm thick.

In certain embodiments, the present invention relates to the aforementioned device, wherein said polyelectrolyte multilayer is less than about 500 nm thick.

In certain embodiments, the present invention relates to the aforementioned device, wherein said polyelectrolyte multilayer is less than about 100 nm thick.

In certain embodiments, the present invention relates to the aforementioned device, wherein said polyelectrolyte multilayer is less than about 10 nm thick.

In certain embodiments, the present invention relates to the aforementioned device, wherein said polyelectrolyte multilayer further comprises a metallic nanocluster.

In certain embodiments, said implantable medical device is a ball and socket joint.

In certain embodiments, said implantable medical device is a ball and socket joint, said polyelectrolyte multilayer comprises poly(acrylic acid) and poly(allylamine hydrochloride).

In certain embodiments, said implantable medical device is a ball and socket joint, said said polyelectrolyte multilayer comprises poly(acrylic acid) and poly(allylamine hydrochloride), and said surface is metal.

In certain embodiments, said implantable medical device is a ball and socket joint, said said polyelectrolyte multilayer comprises poly(acrylic acid) and poly(allylamine hydrochloride), and said surface is ultra-high molecular weight polyethylene.

Method of Preparing a PEM-Coated Medical Device

One aspect of the present invention involves a method of preparing a PEM-coated implantable medical device, comprising the step of:

applying a film to a surface of an implantable medical device, wherein said film comprises a polyelectrolyte multilayer and said surface is glass, metal, plastic, polymer, or fiberglass.

In certain embodiments, the present invention relates to the aforementioned method, wherein said film comprises a linear or branched poly(acrylic acid), poly(allylamine hydrochloride), poly(ethylene imine), poly(diallyldimethylammonium chloride), sulfonated polystyrene, or poly(2-acrylamido-2-methyl-1-propane-sulfonic acid).

In certain embodiments, the present invention relates to the aforementioned method, wherein said film comprises a linear or branched poly(acrylic acid) or poly(allylamine hydrochloride).

In certain embodiments, the present invention relates to the aforementioned method, wherein said film comprises linear or branched poly(acrylic acid) and poly(allylamine hydrochloride).

In certain embodiments, the present invention relates to the aforementioned method, wherein said surface is metal, plastic, or polymer.

In certain embodiments, the present invention relates to the aforementioned method, wherein said surface is metal.

In certain embodiments, the present invention relates to the aforementioned method, wherein said surface is stainless steel.

In certain embodiments, the present invention relates to the aforementioned method, wherein said surface is plastic.

In certain embodiments, the present invention relates to the aforementioned method, wherein said surface is ultra-high molecular weight polyethylene.

In certain embodiments, the present invention relates to the aforementioned method, wherein said surface is metal and said film comprises poly(acrylic acid).

In certain embodiments, the present invention relates to the aforementioned method, wherein said film is less than about 700 nm thick.

In certain embodiments, the present invention relates to the aforementioned method, wherein said film is less than about 500 nm thick.

In certain embodiments, the present invention relates to the aforementioned method, wherein said film is less than about 100 nm thick.

In certain embodiments, the present invention relates to the aforementioned method, wherein said film is less than about 10 nm thick.

In certain embodiments, the present invention relates to the aforementioned method, wherein said film comprises a polyelectrolyte multilayer and a metallic nanocluster.

In certain embodiments, the present invention relates to the aforementioned method, wherein said film comprises a polyelectrolyte multilayer and a silver nanocluster.

In certain embodiments, said implantable medical device is a ball and socket joint.

Method of Reducing Wear Using PEM Film

One aspect of the present invention involves a method of reducing the wear between two contacting materials, comprising the step of:

moving a first material in contact with a second material in an environment, wherein a first surface of said first material is in contact with a second surface of said second material, wherein said first surface, said second surface, or both is coated with a polyelectrolyte multilayer, thereby decreasing the wear of said first material, said second material, or both compared to the wear in the absence of said polyelectrolyte multilayer.

In certain embodiments, the present invention relates to the aforementioned method, wherein said polyelectrolyte multilayer comprises a linear or branched poly(acrylic acid), poly(allylamine hydrochloride), poly(ethylene imine), poly(diallyldimethylammonium chloride), sulfonated polystyrene, or poly(2-acrylamido-2-methyl-1-propane-sulfonic acid).

In certain embodiments, the present invention relates to the aforementioned method, wherein said polyelectrolyte multilayer comprises a linear or branched poly(acrylic acid) or poly(allylamine hydrochloride).

In certain embodiments, the present invention relates to the aforementioned method, wherein said polyelectrolyte multilayer comprises linear or branched poly(acrylic acid) and poly(allylamine hydrochloride).

In certain embodiments, the present invention relates to the aforementioned method, wherein said first material is glass, metal, plastic, or polymer.

In certain embodiments, the present invention relates to the aforementioned method, wherein said first material is glass.

In certain embodiments, the present invention relates to the aforementioned method, wherein said first material is metal.

In certain embodiments, the present invention relates to the aforementioned method, wherein said first material is plastic.

In certain embodiments, the present invention relates to the aforementioned method, wherein said first material is ultra-high molecular weight polyethylene.

In certain embodiments, the present invention relates to the aforementioned method, wherein said second material is glass, metal, plastic, or polymer.

In certain embodiments, the present invention relates to the aforementioned method, wherein said first material is glass and said second material is metal.

In certain embodiments, the present invention relates to the aforementioned method, wherein said first material is plastic and said second material is plastic.

In certain embodiments, the present invention relates to the aforementioned method, wherein said first material is plastic and said second material is metal.

In certain embodiments, the present invention relates to the aforementioned method, wherein said first material is glass and said polyelectrolyte multilayer comprises poly(acrylic acid).

In certain embodiments, the present invention relates to the aforementioned method, wherein said first material is glass and said polyelectrolyte multilayer comprises poly(acrylic acid) and poly(allylamine hydrochloride).

In certain embodiments, the present invention relates to the aforementioned method, wherein said first material is metal and said polyelectrolyte multilayer comprises poly(acrylic acid).

In certain embodiments, the present invention relates to the aforementioned method, wherein said first material is plastic and said polyelectrolyte multilayer comprises poly(acrylic acid).

In certain embodiments, the present invention relates to the aforementioned method, wherein the distal surface of said polyelectrolyte multilayer comprises PAH.

In certain embodiments, the present invention relates to the aforementioned method, wherein said first surface and said second surface is coated with a polyelectrolyte multilayer.

In certain embodiments, the present invention relates to the aforementioned method, wherein said first surface and said second surface is coated with a polyelectrolyte multilayer comprising poly(acrylic acid).

In certain embodiments, the present invention relates to the aforementioned method, wherein said first material is metal, said second material is plastic, and said first surface is coated with a polyelectrolyte multilayer.

In certain embodiments, the present invention relates to the aforementioned method, wherein said first material is plastic, said second material is plastic, and said first surface is coated with a polyelectrolyte multilayer.

In certain embodiments, the present invention relates to the aforementioned method, wherein said first material is glass, said second material is metal, and said first surface and said second surface is coated with a polyelectrolyte multilayer.

In certain embodiments, the present invention relates to the aforementioned method, wherein said first material is plastic, said second material is plastic, and said first surface and said second surface is coated with a polyelectrolyte multilayer.

In certain embodiments, the present invention relates to the aforementioned method, wherein said first material is metal, said second material is plastic, and said first surface and said second surface is coated with a polyelectrolyte multilayer.

In certain embodiments, the present invention relates to the aforementioned method, wherein said polyelectrolyte multilayer is less than about 700 nm thick.

In certain embodiments, the present invention relates to the aforementioned method, wherein said polyelectrolyte multilayer is less than about 500 nm thick.

In certain embodiments, the present invention relates to the aforementioned method, wherein said polyelectrolyte multilayer is less than about 100 nm thick.

In certain embodiments, the present invention relates to the aforementioned method, wherein said polyelectrolyte multilayer is less than about 10 nm thick.

In certain embodiments, the present invention relates to the aforementioned method, wherein said polyelectrolyte multilayer further comprises a metallic nanocluster.

In certain embodiments, the present invention relates to the aforementioned method, wherein said polyelectrolyte multilayer further comprises a silver nanocluster.

In certain embodiments, the present invention relates to the aforementioned method, wherein said environment comprises water or bovine calf serum.

In certain embodiments, the present invention relates to the aforementioned method, wherein said environment comprises synovial joint fluid.

Definitions

For convenience, certain terms employed in the specification, examples, and appended claims are collected here.

The articles "a" and "an" are used herein to refer to one or to more than one (i.e. to at least one) of the grammatical object of the article. By way of example, "an element" means one element or more than one element.

The term "implant" is any object intended for placement in a human body that is not a living tissue. Implants include naturally derived objects that have been processed so that their living tissues have been devitalized. As an example, bone grafts can be processed so that their living cells are removed, but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human body. Representative examples of implants include hip joint replacement implant, knee joint replacement implant, shoulder joint replacement implant, and elbow joint replacement implant The term "medical device" refers to a non-naturally occurring object that is inserted or implanted in a subject or applied to a surface of a subject. Medical devices can be made of a variety of biocompatible materials, including: metals, ceramics, polymers, gels and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate and polyphazenes. Medical devices can also be fabricated using certain naturally-occurring materials or treated naturally-occurring materials. As an example, a heart valve can be fabricated by combining a treated porcine heart valve with an affixation apparatus using artificial materials. Medical devices can include any combination of artificial materials, combinations selected because of the particular characteristics of the components. For example, a hip implant can include a combination of a metallic shaft to bear the weight, a ceramic artificial joint and a polymeric glue to affix the structure to the surrounding bone. An implantable device is one intended to be completely imbedded in the body without any structure left outside the body (e.g. heart valve). An insertable device is one that is partially imbedded in the body but has a part intended to be external (e.g. a catheter or a drain). Medical devices can be intended for short-term or long-term residence where they are positioned. A hip implant is intended for several decades of use, for example. By contrast, a tissue expander may only be needed for a few months, and is removed thereafter.

The term "environment" refers to conditions in which an object is surrounded.

The term "wear" refers to diminishment or decay through use, as described by Marriam Webster's Collegiate Dictionary. 10$^{th}$ Ed. Mish, F. C. 1993.

The term "friction" refers to the force that resists relative motion between two bodies in contact, as described by Marriam Webster's Collegiate Dictionary. 10$^{th}$ Ed. Mish, F. C. 1993.

The term "copolymer" as used herein means a polymer of two or more different monomers.

The term "electrolyte" as used herein means any chemical compound that ionizes when dissolved.

The term "polyelectrolyte" as used herein means a polymeric electrolyte, such as polyacrylic acid.

The term "pH" as used herein means a measure of the acidity or alkalinity of a solution, equal to 7, for neutral solutions and increasing to 14 with increasing alkalinity and decreasing to 0 with increasing acidity.

The term "pH dependent" as used herein means a weak electrolyte or polyelectrolyte, such as polyacrylic acid, in which the charge density can be adjusted by adjusting the pH.

The term "pH independent" as used herein means a strong electrolyte or polyelectrolyte, such as polystyrene sulfonate, in which the ionization is complete or very nearly complete and does not change appreciably with pH.

The term "$K_a$" as used herein means the equilibrium constant describing the ionization of a weak acid.

The term "$pK_a$" as used herein means a shorthand designation for an ionization constant and is defined as $pK_a = -\log K_a$. $pK_a$ values are useful when comparing the relative strength of acids.

The term "multilayer" as used herein means a structure comprised of two or more layers.

The abbreviation "PDMS" as used herein means poly (dimethylsiloxane).

The abbreviation "LPEI" as used herein means linear polyethyleneimine.

The abbreviation "BPEI" as used herein means branched polyethyleneimine.

The term "polyacrylic acid" (PAA) as used herein means a polymer with repeating monomeric units of formula [—$CH_2CH(COO^-)$—].

The term "polyallylamine hydrochloride" (PAH) as used herein means a polymer with repeating monomeric units of formula [—$CH_2CH(CH_2NH_3^+)$—].

The term "polyacrylamide" (PAAm) as used herein means a polymer with repeating monomeric units of formula [—$CH_2CH(CONH_2)$—].

The term "polyrnethacrylic acid" (PMA) as used herein means a polymer with repeating monomeric units of formula [—$CH_2C(CH_3)(COO^-)$—].

The terms "poly(styrene sulfonate)" (PSS) and "sulfonated polystyrene" (SPS) are used interchangeably herein, and refer to a polymer with repeating monomeric units of formula [—$CH_2CH(C_6H_4(SO_3^-))$—].

The term "polydiallyldimethylammonium chloride" (PDAC) as used herein means a polymer with repeating monomeric units of formula

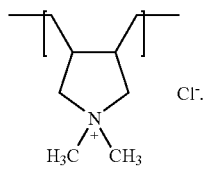

For purposes of this invention, the chemical elements are identified in accordance with the Periodic Table of the Elements, CAS version, Handbook of Chemistry and Physics, 67th Ed., 1986-87, inside cover.

EXEMPLIFICATION

The invention now being generally described, it will be more readily understood by reference to the following examples, which are included merely for purposes of illustration of certain aspects and embodiments of the present invention, and are not intended to limit the invention.

Example 1

Preparation of Polyelectrolyte Multilayer Films

PAH ($M_W$=70000) was purchased from Sigma-Aldrich (Milwaukee, Wis.). PAA ($M_W$=90000) was obtained from Polysciences (Warrington, Pa.). Both these polymers were used without further purification. Deionized water (>18 MΩ cm, Millipore Milli-Q) was used for preparation of all aqueous solutions, and during rinsing procedures.

Bovine calf serum (79 g/L total protein), employed as a lubricant solution in certain tests, was purchased from JRH Biosciences (Lenexa, Kans.). The serum was diluted to 23 g/L using deionized water, following recommended procedures. See A. Wang, A. Essner, V. K. Polineni, D. C. Sun, C. Stark and J. H. Dumbleton, Lubrication and wear of ultra-high molecular weight polyethylene in total joint replacements, in: I. M. Hutchings (Ed.), New Directions in Tribology, Mechanical Engineering Publications Limited, Bury St Edmunds, UK, 443-458, 1997. The solution also contained 20 mM of the sodium salt of ethylenediaminetetraacetic acid (EDTA), and 0.2% by weight of sodium azide. Both these chemicals were obtained from Sigma-Aldrich (Milwaukee, Wis.).

Stainless steel sheets (type 316, #8 mirror finish), with an average roughness of approximately 6 nm, were purchased from McMaster-Carr (Dayton, N.J.). Polished silicon wafers of <111> orientation were obtained from WaferNet (San Hose, Calif.). Glass microscope slides from VWR Scientific Inc. (West Chester, Pa.) were used. The average roughness for both the glass and silicon substrates was less than 1 nm. These materials were all used, as received, as substrates for PEM assembly.

Stainless steel, glass, and silicon slides were degreased in a detergent solution, via ultrasonication, for 15 minutes followed by ultrasonication in water for 10 minutes. After further rinsing them in water, the slides were subjected to air-plasma treatment (5 min at 100 W-Harrick Scientific PDC-32G plasma cleaner/sterilizer). PAH and PAA aqueous solutions (0.01 M based on molecular weights of the repeat unit) were adjusted to the desired pH using 1 M HCl or 1 M NaOH. The PEMs were formed by immersing the slides into the PAH solution for 15 minutes, followed by three rinsing steps in water for 2, 1, and 1 minute respectively. The substrates were then immersed in the PAA solution for 15 minutes followed by identical rinsing steps; this process built a "bilayer". The cycle was repeated to build PEMs of the desired thickness. The immersion and rinsing steps were performed using an automated Zeiss HMS programmable slide stainer. See D. Yoo, S. S. Shiratori, and M. F. Rubner *Macromolecules* 1998, 31, 4309-4318. The PEM-coated substrates were finally dried by flushing with air at room temperature, and stored at ambient conditions for several hours before tribological testing. The films were assembled at a pH of 7.5 or 3.5 for the PAH assembly solution, and a pH of 3.5 for PAA, referred to as (PAH 7.5/PAA 3.5) or (PAH 3.5/PAA 3.5). The thickness of the PEMs, on glass substrates, was measured using a Tencor P-10 surface profiler.

Example 2

Biaxial Compression/Shear Test

Friction and wear behavior of PEMs was studied using a prototype meso/micro-scale flexure-based biaxial testing apparatus (FIG. 3); details about the machine are given in reference. See B. P. Gearing and L. Anand, A novel testing apparatus for tribological studies at the small scale, 2001 ASME International Mechanical Engineering Congress and Exposition, New York, N.Y., USA, 2001. The normal force in this apparatus is controlled with a resolution of 80 μN over a range of 3.5 N. The shear force is measured with a resolution of 225 μN. Tangential displacements can be imposed in steps of 4 nm ranging from 0.5 µm/s to 600 µm/s. The entire system is mounted on a vibration-isolated table to minimize extraneous disturbances.

Figure 3:
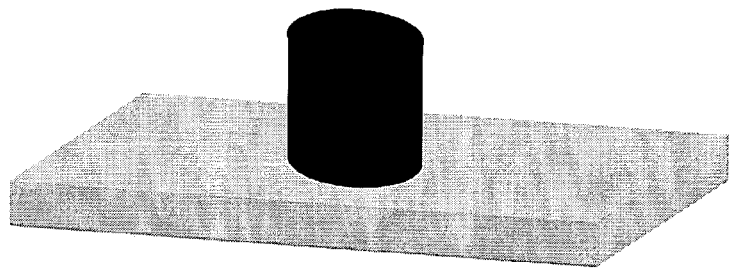
FIG. 3 depicts the mating surfaces used in the flexure-based biaxial apparatus.

Flat-on-flat configurations were used for all tests. The apparatus is designed to hold the upper, smaller surface (a 1 mm or 2 mm diameter pin in this study) stationary, while the lower, larger block is subject to reciprocating motion. Coated and uncoated glass, silicon, and stainless steel slides were mounted on the lower surface using double-coated paper scotch tape. The upper pin counterface was made of D2 hardened tool steel or type 316 stainless steel. It was either uncoated, or coated directly with the PEM films; in cases when an uncoated pin was articulated against the lower slider, it was polished to an average roughness of 1 µm using aluminum oxide film-coated disks. The polished pin was subsequently cleaned with acetone, and dried in a blast of air. A schematic of the mating surfaces used in this study is depicted in FIG. 3.

In all tests, the mating surfaces were subject to reciprocating motion over a 3 mm path length. The number of cycles was restricted to a maximum of 30, corresponding to an accumulated sliding distance of 180 mm. The sliding speed was 200 µm/s in all experiments. No effort was made to control the humidity in the test area; the ambient humidity levels were in the 15-55% range over the duration of the experimental runs.

Example 3

Pin-On-Disk Wear Test

Wear experiments were also carried out on a macroscale AMTI (Watertown, Mass.) Orthopod pin-on-disk wear-testing machine. Type 304 stainless steel pins, 9 mm in diameter and 25 mm long, were machined to a hemispherical base with a point contact; they were subsequently polished, first using polishing paper, and then against a buffing compound, to obtain a mirror finish. The pin was made to articulate against coated and uncoated glass slides for approximately 2000 cycles of reciprocating motion at a normal load of 3.5 N. A path length of 2 cm, and a frequency of 1 Hz were used for all tests. Between tests, the pins were re-polished, and cleaned with water and ethanol, before drying in a stream of air.

Example 4

Wear Track Analysis

Wear tracks, obtained during tribological tests using the apparatuses described above, were examined using an optical microscope (FIGS. 7-12). In addition, wear was characterized in terms of the topography of the wear track using a profilometer. The wear track was examined at three different points and a representative profile was chosen; in all cases, the surface profiles at different points along the wear track closely resembled each other.

Example 5

Friction Analysis of Polyelectrolyte Multilayer

Materials: PAH ($M_w$=70000) was obtained from Sigma-Aldrich (Milwaukee, Wis.). PAA ($M_w$=90000) was obtained from Polysciences (Warrington, Pa.). These chemicals were used without further purification. Deionized water (>18 MΩ cm, Millipore Milli-Q) was exclusively used in all aqueous solutions and rinsing procedures.

UHMWPE (GUR 1050, Ticona, Bayport, Tex.) rod stock was purchased from Poly Hi Solidur Inc. (Fort Wayne, Ind.). Bars 1 cm×1 cm×7 cm were machined out of the rod stock. The bars were heated to 150° C. in a hydraulic press (Carver, Inc.); this was followed by pressing between two mirror-finish steel plates at approximately 4000 psi for 30 min. The sheets (1 mm thick) were allowed to cool to 90° C. before using cooling water to lower the temperature to 25° C. These sheets were used as substrates for film formation and subsequent tribological testing. Polyelectrolyte Multilayer Film (PEM) Formation: UHMWPE sheets and glass microscope slides were degreased in a detergent solution followed by air plasma treatment (5 min at 100 W; Harrick Scientific PDC-32G plasma cleaner/sterilizer). PAH and PAA aqueous solutions (0.01 M based on molecular weights of the repeat unit) were adjusted to the desired pH using 1 M HCl or 1 M NaOH. The PEMs were formed by immersing the slides into the PAH solution for 15 min followed by three rinsing steps in water for 2.1, and 1 min respectively. The substrates were then immersed in the PAA solution for 15 min followed by identical rinsing steps. The immersions and rinsing steps were performed using an automated Zeiss HMS slide stainer. See Yoo, D.; Shiratori, S. S.; Rubner, M. F. *Macromol.* 1998, 31, 4309. The PEM was finally dried in air (room temperature) and stored at ambient conditions.

Friction Tests: Friction tests on glass and UHMWPE slides, with and without PEMs, were conducted using a flexure-based biaxial compression/shear apparatus. See Gearing, B. P.; Anand, L. *Proc. ASME Int. Mech. Eng. Congress and Exposition* 2001. The normal force in this apparatus is controlled with a resolution of 80 µN over a range of 5 N. The shear force is measured with a resolution of 225 µN; displacement rates than can be imposed range from 0.5 µm/s to 600 µm/s. The entire system rests on a vibration-isolated table to minimize environmental disturbances.

For friction tests on glass (FIG. 13), a flat-on-flat configuration was used; the sliding counterface was a steel block, polished using a 1 µm alumina slurry. A load of 2 N, corresponding to a nominal stress of 20 kPa, was employed. For non-coated and coated UHMWPE slides, a pin-on-flat configuration with a normal load of 3.1 N (4 Mpa nominal stress) was used. The pin, 1 mm in diameter, was also polished using the same slurry. The counterfaces were subjected to reciprocating motion with a path length of 3 mm. The sliding speed was confined to 200 µm/s. 30 cycles, with a total sliding distance of approximately 180 mm, were used for all tests. In between tests, the steel counterfaces were cleaned with 5 M saline solution (to remove any PEMs that might have formed a transfer film), followed by water and acetone; they were dried using an inert gas.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of reducing the wear between two contacting materials, comprising the step of:

moving a first material in contact with a second material in an environment, wherein a first surface of said first material is in contact with a second surface of said second material, wherein said first material is glass, metal, plastic, or polymer; said second material is glass, metal, plastic, or polymer; and said first surface, said second surface, or both surfaces is coated with a polyelectrolyte multilayer, wherein said polyelectrolyte multilayer consists essentially of a plurality of alternating layers of polyelectrolyte, wherein each alternating layer of polyelectrolyte is independently selected from the group consisting of a linear or branched poly(acrylic acid), poly(allylamine hydrochloride), poly(ethylene imine), sulfonated polystyrene, and poly(2-acrylamido-2-methyl-1-propanesulfonic acid);

thereby decreasing the wear of said first material, said second material, or both materials compared to the wear in the absence of said polyelectrolyte multilayer.

2. The method of claim 1, wherein said polyelectrolyte multilayer comprises a linear or branched poly(acrylic acid) or poly(allylamine hydrochloride).

3. The method of claim 1, wherein said polyelectrolyte multilayer comprises linear or branched poly(acrylic acid) and poly(allylamine hydrochloride).

4. The method of claim 1, wherein said first material is glass.

5. The method of claim 1, wherein said first material is metal.

6. The method of claim 1, wherein said first material is plastic.

7. The method of claim 1, wherein said first material is ultra-high molecular weight polyethylene.

8. The method of claim 1, wherein said first material is glass and said second material is metal.

9. The method of claim 1, wherein said first material is plastic and said second material is plastic.

10. The method of claim 1, wherein said first material is plastic and said second material is metal.

11. The method of claim 1, wherein said first material is glass and said polyelectrolyte multilayer comprises poly(acrylic acid).

12. The method of claim 1, wherein said first material is glass and said polyelectrolyte multilayer comprises poly(acrylic acid) and poly(allylamine hydrochloride).

13. The method of claim 1, wherein said first material is metal and said polyelectrolyte multilayer comprises poly(acrylic acid).

14. The method of claim 1, wherein said first material is plastic and said polyelectrolyte multilayer comprises poly(acrylic acid).

15. The method of claim 1, wherein the distal surface of said polyelectrolyte multilayer comprises poly(allylamine hydrochloride).

16. The method of claim 1, wherein said first surface and said second surface is coated with a polyelectrolyte multilayer.

17. The method of claim 1, wherein said first surface and said second surface is coated with a polyelectrolyte multilayer comprising poly(acrylic acid).

18. The method of claim 1, wherein said first material is metal, said second material is plastic, and said first surface is coated with a polyelectrolyte multilayer.

19. The method of claim 1, wherein said first material is plastic, said second material is plastic, and said first surface is coated with a polyelectrolyte multilayer.

20. The method of claim 1, wherein said first material is glass, said second material is metal, and said first surface and said second surface is coated with a polyelectrolyte multilayer.

21. The method of claim 1, wherein said first material is plastic, said second material is plastic, and said first surface and said second surface is coated with a polyelectrolyte multilayer.

22. The method of claim 1, wherein said first material is metal, said second material is plastic, and said first surface and said second surface is coated with a polyelectrolyte multilayer.

23. The method of claim 1, wherein said polyelectrolyte multilayer is less than about 700 nm thick.

24. The method of claim 1, wherein said polyelectrolyte multilayer is less than about 500 nm thick.

25. The method of claim 1, wherein said polyelectrolyte multilayer is less than about 100 nm thick.

26. The method of claim 1, wherein said polyelectrolyte multilayer is less than about 10 nm thick.

27. The method of claim 1, wherein said polyelectrolyte multilayer further comprises a metallic nanocluster.

28. The method of claim 1, wherein said polyelectrolyte multilayer further comprises a silver nanocluster.

29. The method of claim 1, wherein said environment comprises water or bovine calf serum.

30. The method of claim 1, wherein said environment comprises synovial joint fluid.

* * * * *